United States Patent [19]
Tamura et al.

[11] Patent Number: 5,574,178
[45] Date of Patent: Nov. 12, 1996

[54] 4,6-DI-T-BUTYL-DIHYDROBENZOFURAN-5-OL AND ITS DERIVATIVES

[75] Inventors: Kunio Tamura; Yoshiaki Kato; Mitsutaka Yoshida; Osamu Cynshi; Yasuhiro Ohba, all of Shizuoka, Japan

[73] Assignee: Chugai Seiyaku Kabushiki Kaisha, Tokyo, Japan

[21] Appl. No.: 416,862

[22] PCT Filed: Oct. 18, 1993

[86] PCT No.: PCT/JP93/01489

§ 371 Date: Apr. 17, 1995

§ 102(e) Date: Apr. 17, 1995

[87] PCT Pub. No.: WO94/08930

PCT Pub. Date: Apr. 28, 1994

[30] Foreign Application Priority Data

Oct. 16, 1992 [JP] Japan ................................. 4-321101

[51] Int. Cl.⁶ ..................................................... C07D 307/79
[52] U.S. Cl. ............................ 549/462; 549/336; 568/650
[58] Field of Search ................................................ 549/462

[56] References Cited

U.S. PATENT DOCUMENTS

| | | | |
|---|---|---|---|
| 4,857,516 | 8/1989 | Terao et al. | 549/462 |
| 4,966,907 | 10/1990 | Caldwell et al. | 549/462 |
| 4,966,973 | 10/1990 | Goto et al. | 549/462 |
| 4,978,761 | 12/1990 | Goto et al. | 549/462 |
| 4,999,350 | 3/1991 | Brufani et al. | 549/462 |
| 5,041,568 | 8/1991 | Brufani et al. | 549/462 |
| 5,091,533 | 2/1992 | Belanger et al. | 544/318 |

FOREIGN PATENT DOCUMENTS

| | | |
|---|---|---|
| 1-272578 | 10/1989 | Japan . |
| 2-78675 | 3/1990 | Japan . |
| 2-76870 | 3/1990 | Japan . |
| 2-76869 | 3/1990 | Japan . |
| 2-121975 | 5/1990 | Japan . |
| 4-300878 | 10/1992 | Japan . |
| 5-105675 | 4/1993 | Japan . |
| 5-178848 | 7/1993 | Japan . |
| 6-505732 | 6/1994 | Japan . |
| WO92/16485 | 10/1992 | WIPO . |
| WO93/09777 | 5/1993 | WIPO . |
| WO93/20057 | 10/1993 | WIPO . |

OTHER PUBLICATIONS

Zambias et al, A Convenient Synthesis of 4–ter–Butyl–5–benzofuranols and Dihydrobenzofuranols, J. Org. Chem., vol. 53, pp. 4135–4137, 1988.

Mukai et al, Synthesis and Kinetic Study of Antioxidant Activity of New Tocopherol (Vitamin E) Compounds, J. Org. Chem., vol. 54, pp. 552–556, 1989.

Hammond et al, 2,3–Dihydro–5–benzofuranols as Antioxidant–Based Inhibitors of Leukotriene J. Med. Chem., vol. 32, No. 5, pp. 1006–1021, 1989.

Burton et al, Autoxidation of Biological Molecules. 4. Maximizing the Antioxidant Activity of Phenols, J. AM. Chem. Soc., vol. 107, pp. 7053–7065, 1985.

*Primary Examiner*—Bernard Dentz
*Attorney, Agent, or Firm*—Browdy and Neimark

[57] ABSTRACT

Compounds represented by the general formula as well as intermediates for the synthesis of thereof:

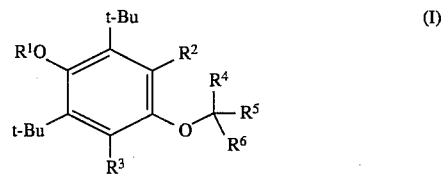

(I)

where $R^1$ is a hydrogen atom or an acyl group; $R^2$ is a lower alkyl group; $R^3$ is a hydrogen atom or a lower alkyl group; $R^4$, $R^5$ and $R^6$, which may be the same or different, are a hydrogen atom or an optionally substituted alkyl, alkenyl, alkynyl or aryl group; $R^2$ and $R^4$, when taken together, may form a 5-membered ring; $R^5$ and $R^6$, when taken together, may form a cycloalkyl group or a heterocyclic group in which at least one methylene on the ring of a cycloalkyl group is substituted by an oxygen atom, a sulfur atom or an alkyl-substituted nitrogen atom, provided that $R^6$ is not present if the ring formed by $R^2$ and $R^4$ taken together is a benzofuran ring. The compounds represented by the general formula (I) have a highly selective anti-oxidative activity and are useful as therapeutics of ischemic diseases such as arteriosclerosis and myocardial infarction.

9 Claims, No Drawings

4,6-DI-T-BUTYL-DIHYDROBENZOFURAN-5-OL AND ITS DERIVATIVES

This application is a 371 of PCT/JP93/01489 filed Oct. 18, 1993 and published as WO94/08930 Apr. 28, 1994.

TECHNICAL FIELD

This invention relates to compounds for preventing the oxidative modification of LDL, particularly, to compounds useful as therapeutics of arteriosclerosis, myocardial infarction and other ischemic diseases. More specifically, the invention relates to compounds represented by the following general formula (I), as well as compounds represented by the general formula (II) which are useful intermediates for the synthesis of compounds (I):

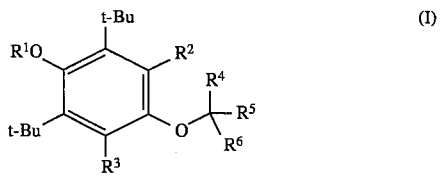

(where $R^1$ is a hydrogen atom or an acyl group; $R^2$ is a lower alkyl group; $R^3$ is a hydrogen atom or a lower alkyl group; $R^4$, $R^5$ and $R^6$, which may be the same or different, are a hydrogen atom or an optionally substituted alkyl, alkenyl, alkynyl or aryl group; $R^2$ and $R^4$, when taken together, may form a 5-membered ring; $R^5$ and $R^6$, when taken together, may form a cycloalkyl group or a heterocyclic group in which at least one methylene on the ring of a cycloalkyl group is substituted by an oxygen atom, a sulfur atom or an alkyl-substituted nitrogen atom, provided that $R^6$ is not present if the ring formed by $R^2$ and $R^4$ taken together is a benzofuran ring);

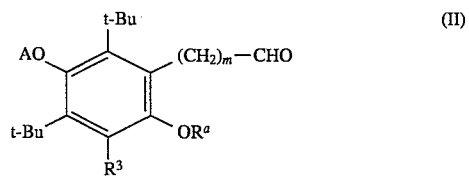

(where $R^3$ has the same meaning as defined above; A is a protective group; $R^a$ is a hydrogen atom or a lower alkyl group; and m is an integer of 0 or 1).

BACKGROUND ART

Atherosclerosis is one of the principal causes of ischemic diseases such as angina pectoris, myocardial infarction and cerebral apoplexy. The mechanism of initiation and progression of atherosclerosis is closely related to the oxidative modification of LDL. The modified LDLs are not recognized by the LDL receptor but by the scavenger receptor, to induce the foam cell formation which is characterized by cholesterol accumulation.

The modification of LDL is caused by endothelial cells, smooth muscle cells, macrophages, etc. and the modified LDLs are eventually taken by macrophages via the scavenger or other pathways. It is additionally known that the modification of LDL by these cells is similar to the oxidative modification of LDL by $Cu^{2+}$.

LDL is chiefly composed of cholesterol esters, phospholipids and apo-B-100. The oxidative modification of LDL is shown from various aspects, for example fragmentation of apo-B-100 by the generated radicals, the reaction between the lipid peroxidation products and the free amino groups in apo-B-100 lysine residues, and the transformation of phosphatidyl choline to a lyso-form. One of the most established phenomena in LDL oxidation is an increase of thiobarbituric acid reactive substances (TBARS) as a result of the lipid peroxidation. Oxidized LDL, or LDL that has undergone such oxidative modification, causes the foam cell formation and the cholesterol accumulation by the scavenger and other pathways.

Under these circumstances, it is expected that compounds having the inhibitory action on lipid peroxidation can inhibit the initiation and progression of atherogenic lesions by preventing the oxidative modification of LDL and, hence, have the potential to work as therapeutics of arteriosclerosis.

In ischemic diseases such as cerebral apoplexy and myocardial infarction, various active oxygen species are generated during blood reperfusion at ischemic sites and tissue disorders can be exacerbated by the disruption of cell membranes and other effects caused by the lipid peroxidation. It is expected that compounds having the anti-oxidative activity can prevent the tissue disorders in ischemic lesions by removing the various active oxygen species and lipid peroxidation and, hence, have the potential to work as therapeutics of ischemic diseases.

Vitamin E is known as a natural antioxidant and studies have been made to develop synthetic antioxidants using vitamin E as the basic skeleton but no completely satisfactory products have yet been synthesized.

Some of the compounds of the present invention which are represented by the general formula (I) have been reported in the official gazette of Japanese Patent Publication (kokai) No. Hei 2-121975, in which the generic concept of those particular compounds is expressed by the general formula (III):

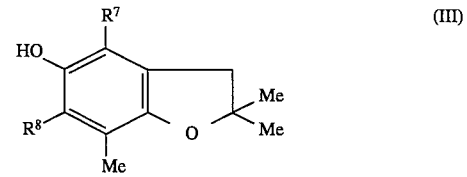

(where $R^7$ is a straight or branched lower alkyl group having 2-4 carbon atoms; $R^8$ is a straight or branched lower alkyl group having 1-4 carbon atoms).

Another part of the compounds of the present invention are described, by their generic concept, in Japanese Patent Publication (kokai) No. Hei 2-76869, U.S. Pat. No. 4,966,907, etc.

DISCLOSURE OF INVENTION

An object of the present invention is to provide antioxidants useful in the treatment of arteriosclerosis and other ischemic diseases such as myocardial infarction and cerebral apoplexy, as well as intermediates useful for producing said compounds.

We postulated that the reason for the inadequate efficacy of existing antioxidants such as the compounds described in the official gazette of Japanese Patent Publication (kokai) No. Hei 2-121975 was that their activity was lost before they reached the target sites. Because they easily react with various free radical species besides lipid peroxidation related radicals. Based on this assumption, we conducted intensive studies with a view to developing efficient antioxidants having higher reaction specificity; as a result, we found that the compounds represented by the general formula (I) attained our intended object. The present invention has been accomplished on the basis of this finding. We also found that the compounds represented by the general formula (II) were undocumented, novel compounds, which were useful as intermediates for the synthesis of the compounds represented by the general formula (I).

It should be mentioned that the compounds of the invention which are represented by the general formula (I) have the following three characteristic features:

(1) They are lipid-soluble antioxidants which inhibit lipid peroxidation efficiently;

(2) While there are many species of free radicals that are involved in oxidation, the compounds react efficiently with those radical species which are responsible for the chain reaction of lipid peroxidation, therefore they inhibit lipid peroxidation intensely.

(3) In order to develop the specific lipid peroxidation inhibiting action to be specific in lipids, the compounds have low reactivity for so-called "active oxygen" species (e.g. superoxides and singlet oxygen) in aqueous solution.

The compounds of the present invention which are represented by the general formula (I) have two t-butyl groups in both ortho-positions of the phenolic hydroxyl group and they are undocumented novel compounds. Some of the compounds of the present invention are represented by the general formula (III) in the official gazette of Japanese Patent Publication (kokai) No. Hei 2-121975 to express their generic concept; another part of the compounds of the present invention are expressed in terms of their generic concept in Japanese Patent Publication (kokai) No. Hei 2-76869 and U.S. Pat. No. 4,966,907; however, the compounds of the present invention are not described specifically in these patents.

The present invention is based on the fact that the compounds represented by the general formula (I) which have two t-butyl groups in both ortho-positions of the phenolic hydroxyl group exhibit by far superior effects than the compounds represented by the general formula (III) and those described in Japanese Patent Publication (kokai) No. Hei 2-76869 and U.S. Pat. No. 4,966,907, as will be demonstrated by test cases to be described later in this specification.

In the compounds of the invention, the acyl group as $R^1$ may be exemplified by acetyl, formyl, propionyl, benzoyl, benzyloxycarbonyl, etc., with acetyl being preferred. The lower alkyl group as $R^2$ and $R^3$ or $R^a$ refers to a straight or branched alkyl group having 1–6 carbon atoms, as exemplified by methyl, ethyl, n-propyl, i-propyl, n-butyl, s-butyl, t-butyl, etc. The alkyl group as $R^4$, $R^5$ and $R^6$ refers to a straight or branched alkyl group having 1–20 carbon atoms, as exemplified by methyl, ethyl, n-propyl, i-propyl, n-butyl, s-butyl, t-butyl, pentyl, hexyl, heptyl, octyl, nonyl, decyl, etc. The alkenyl group as $R^4$, $R^5$ and $R^6$ refers to a straight or branched alkenyl group having 2–20 carbon atoms, as exemplified by vinyl, allyl, butenyl, pentenyl, geranyl, farnesyl, etc. The alkynyl group as $R^4$, $R^5$ and $R^6$ refers to a straight or branched alkynyl group having 2–20 carbon atoms, as exemplified by ethynyl, propynyl, butynyl, etc. The aryl group as $R^4$, $R^5$ and $R^6$ means a monovalent substituent that is an aromatic hydrocarbon minus a hydrogen atom, as exemplified by phenyl, tolyl, xylyl, biphenyl, naphthyl, anthryl, phenanthryl, etc. Carbon atoms on the ring of the aryl group may be substituted by one or more species such as a halogen atom, a lower alkyl group, a hydroxyl group, an alkoxy group, an amino group, a nitro group, a trifluoromethyl group, etc. Exemplary substituents include a halogen atom, a hydroxyl group, an amino group, an alkoxy group, an aryloxy group, etc. The 5-membered ring which may be formed by $R^2$ and $R^4$ taken together is exemplified by a furan ring and a dihydrofuran ring, which are taken together with the adjacent benzene ring to form a benzofuran ring and a dihydrobenzofuran ring, respectively. The cycloalkyl group which may be formed by $R^5$ and $R^6$ taken together refers to a cycloalkyl group having 3–8 carbon atoms, as exemplified by cyclopropyl, cyclobutyl, cyclopentyl, cyclohexyl, cycloheptyl, cyclooctyl, etc. The heterocyclic group which may be formed by $R^5$ and $R^6$ taken together and in which at least one methylene on the ring of a cycloalkyl group is substituted by an oxygen atom, a sulfur atom or an alkyl-substituted nitrogen atom may be exemplified by a tetrahydropyranyl group. The protective group as A may be exemplified by acetyl, benzoyl, methyl, methoxymethyl, methoxyethoxymethyl, benzyl, trimethylsilyl, benzyloxycarbonyl, tetrahydropyranyl, 2-trimethylsilyl)ethoxymethyl, etc., with acetyl being preferred.

BEST MODE FOR CARRYING OUT THE INVENTION

The compounds of the present invention may typically be synthesized by the following methods.

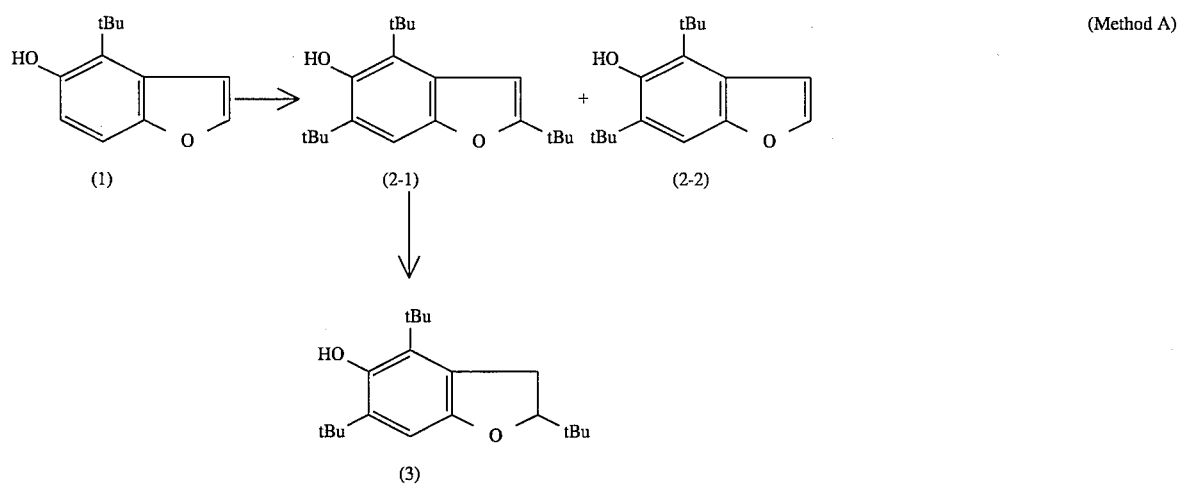

(Method A)

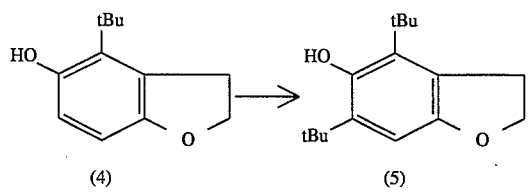
(Method B)
(Method C)
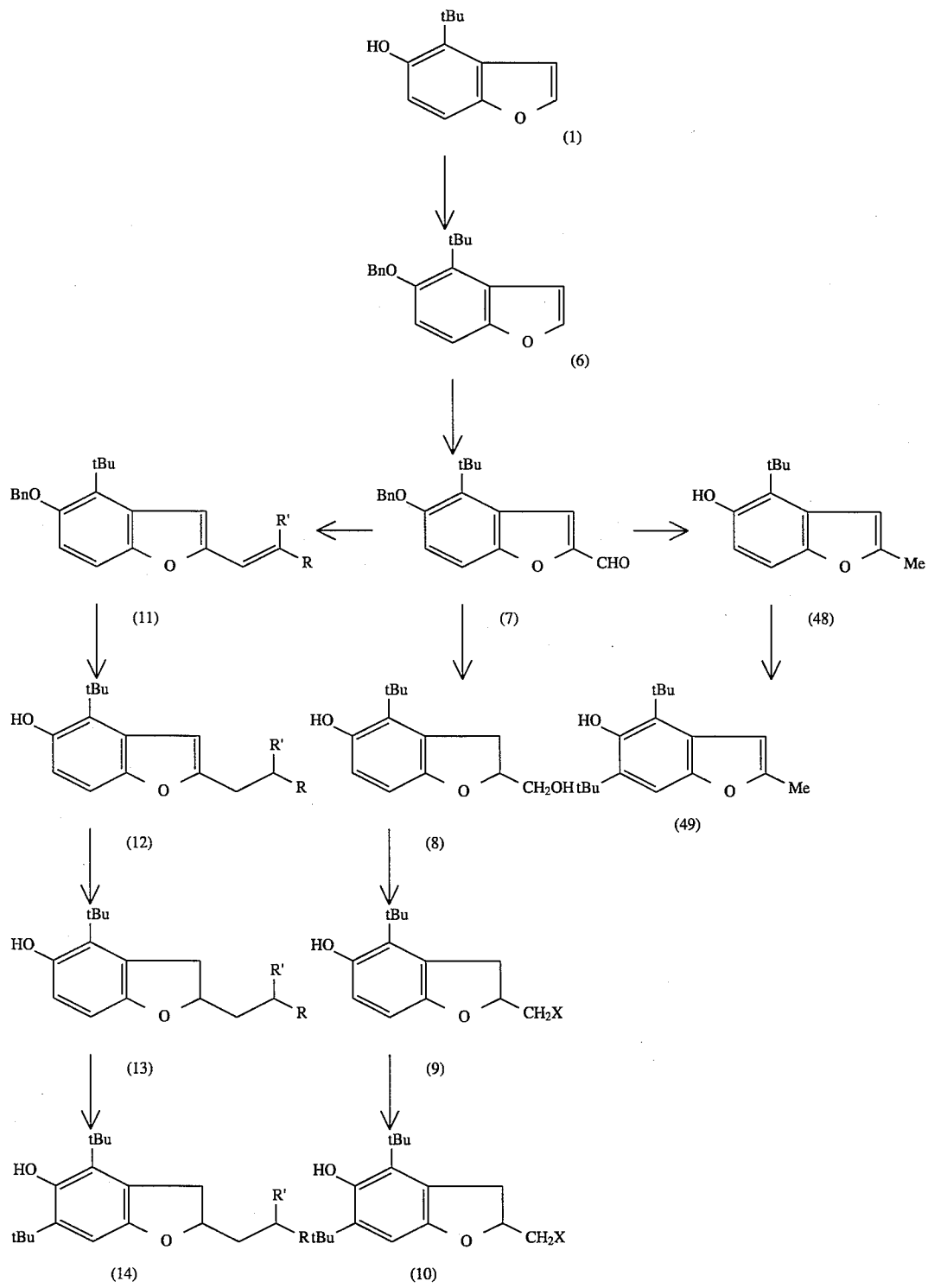

(where X is a halogen atom; R and R', which may be the same or different are an optionally substituted alkyl or aryl group).
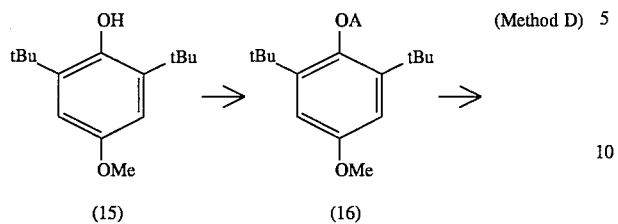
(Method D)
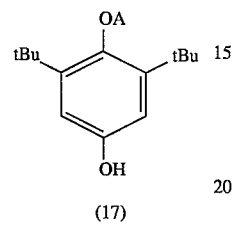
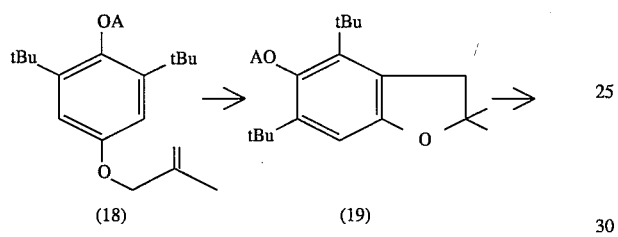
(where A is a protective group).
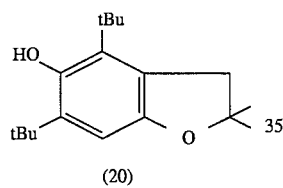
(Method E)
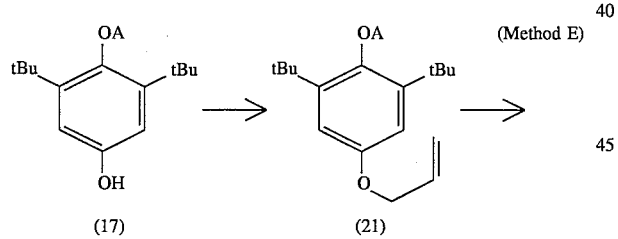
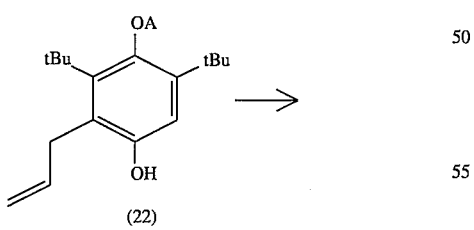
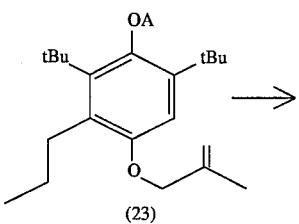
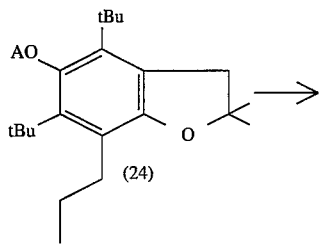
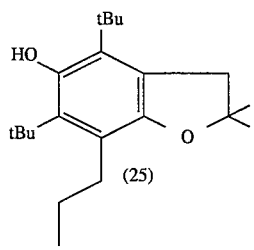
(where A is a protective group).
(Method F)
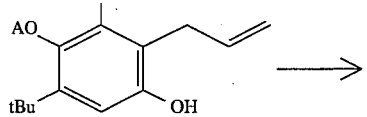
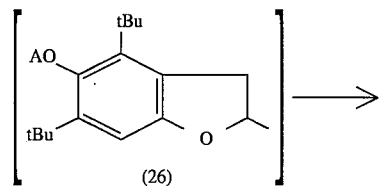
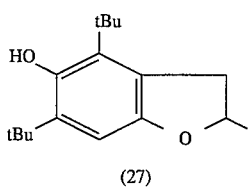
(where A is a protective group).

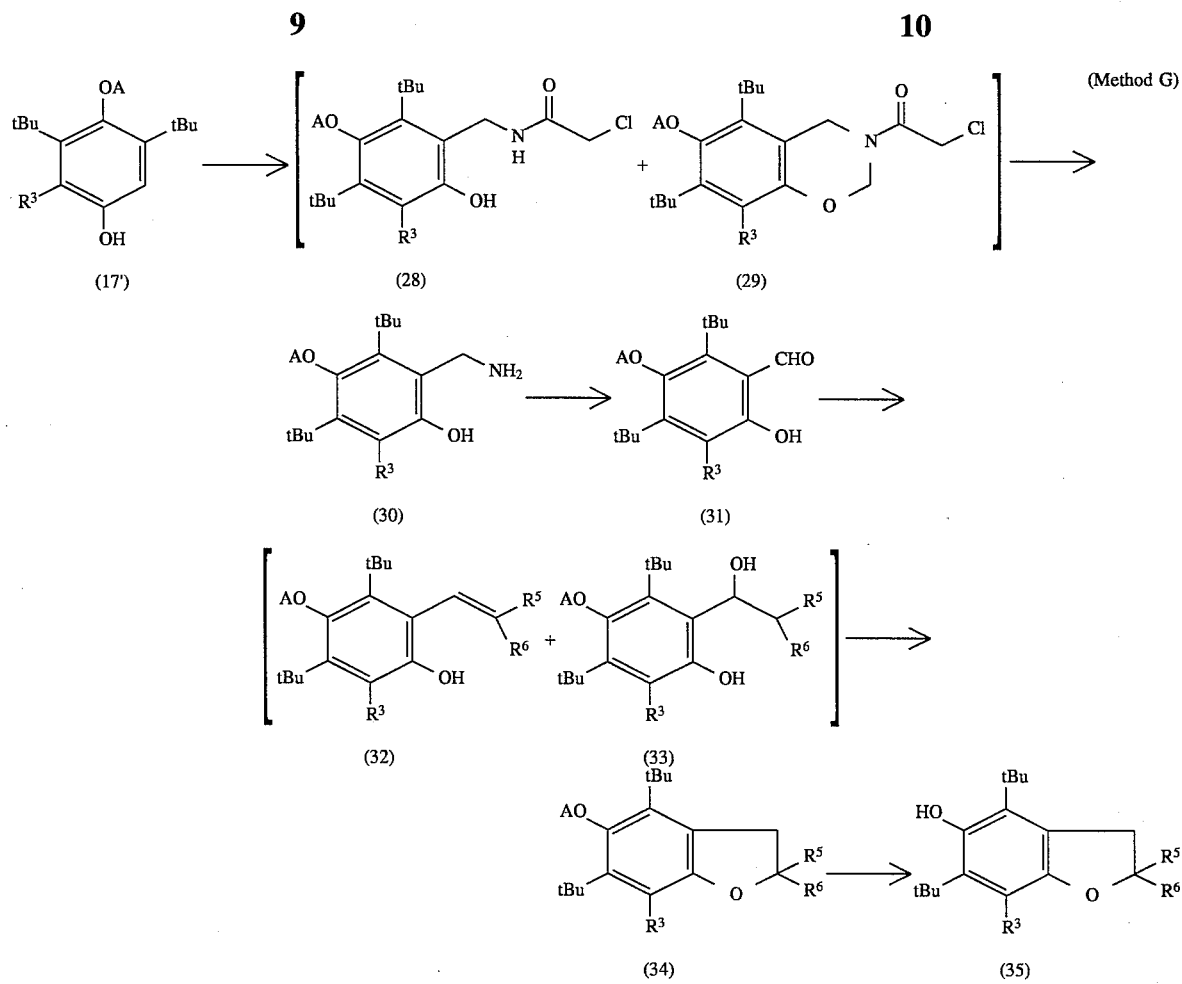

(where A is a protective group; $R^3$, $R^5$ and $R^6$ have the same meanings as defined above).

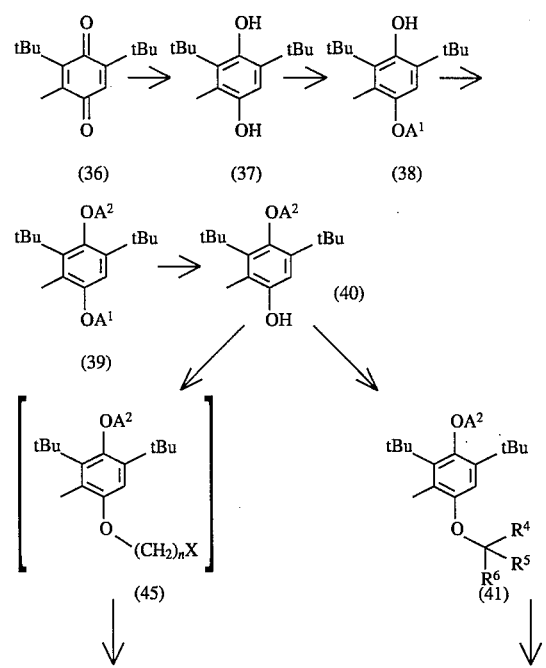

(where $A^1$ and $A^2$ are each a protective group; n is an integer of 3–10).

In method A, the reaction for producing the compounds of formulae (2-1) and (2-2) from the compound of formula (1) is carried out by adding methanesulfonic acid to the compound of formula (1) (see J. Org. Chem., 53, 4135, 1988) and t-butanol in a solvent such as chloroform or dichloromethane at a temperature ranging from −20° C. to room temperature and then stirring the mixture. Conversion from formula (2-1) to formula (3) may typically be accomplished by reduction that involves adding triethylsilane and trifluoroacetic acid to the compound of formula (2-1).

In method B, the reaction for producing the compound of formula (5) from the compound of formula (4) is carried out by adding methanesulfonic acid to the compound of formula (4) (see J. Org. Chem., 53, 4135, 1988) and t-butanol in a solvent such as chloroform or dichloromethane at a temperature ranging from −20° C. to room temperature and then stirring the mixture.

In method C, the reaction for producing the compound of formula (6) from the compound of formula (1) is carried out by adding benzyl bromide to the compound of formula (1) in a solvent such as ether, tetrahydrofuran, N,N-dimethylformamide, N,N-dimethylacetamide or acetone in the presence of a base such as potassium carbonate, sodium carbonate, sodium hydroxide or potassium hydroxide at a temperature of 0°–50° C. and then stirring the mixture. To obtain the compound of formula (7) from the compound of formula (6), formylation is performed with a suitable reagent such as a Vilsmeier reagent. The compound of formula (7) is reduced catalytically to yield the compound of formula (8), which is then treated with a halogenating agent such as thionyl chloride or thionyl bromide for conversion to the compound of formula (9) which, in turn, is processed as in method B to yield the compound of formula (10).

To obtain the compound of formula (14) from the compound of formula (7), the latter compound is first subjected to the Wittig reaction or the like for transformation to the compound of formula (11), which is then reduced catalytically to give the compound of formula (12). The compound of formula (12) is reduced typically by a reaction using triethylsilane and trifluoroacetic acid to afford the compound of formula (13) which, in turn, is processed as in method B to yield the compound of formula (14).

To obtain the compound of formula (49) from the compound of formula (7), the latter is first reduced catalytically to afford the compound of formula (48) which, in turn, is processed as in method B to yield the compound of formula (49).

In method D, the compound of formula (15) is protected at the phenolic hydroxyl group to afford the compound of formula (16), which is demethylated typically with trimethylsilyl iodide to afford the compound of formula (17). The compound of formula (17) is treated with an alkenyl halide such as 3-chloro-2-methyl-1-propene in a solvent such as tetrahydrofuran, N,N-dimethylformamide, N,N-dimethylacetamide or acetone in the presence of a base such as sodium hydride, potassium carbonate, sodium carbonate, sodium hydroxide or potassium hydroxide to afford the compound of formula (18) which, in turn, is subjected to rearrangement by heating in a solvent such as N,N-dimethylaniline to afford the compound of formula (19), which may be deprotected as required to yield the compound of formula (20).

In method E, the reaction for producing the compound of formula (25) from the compound of formula (17) starts with adding an alkenyl halide such as 3-bromo-1-propene to the compound of formula (17) in a solvent such as tetrahydrofuran, N,N-dimethylformamide, N,N-dimethylacetamide or acetone in the presence of a base such as sodium hydride, potassium carbonate, sodium carbonate, sodium hydroxide or potassium hydroxide to afford the compound of formula (21), which is then subjected to rearrangement by heating in a solvent such as N,N-dimethylaniline so that it is transformed to the compound of formula (22). After catalytic reduction, the compound of formula (22) is processed as in the steps of method D for affording the compounds of formulae (18), (19) and (20) from the compound of formula (17), thereby yielding the compounds of formulae (23), (24) and (25).

In method F, the reaction for producing the compound of formula (27) from the compound of formula (22) comprises dissolving the latter compound in a solvent such as chloroform or dichloromethane, allowing a Lewis acid such as boron trifluoride etherate to act on the solution, thereby affording the compound of formula (26), and optionally deprotecting it to yield the compound of formula (27).

In method G, the reaction for producing the compound of formula (30) from the compound of formula (17') comprises dissolving the latter compound in hydrochloric acid, sulfuric acid, acetic acid or a mixture thereof, adding N-hydroxymethyl-2-chloroacetamide to the resulting solution at 0°–50° C., preferably at room temperature, stirring the mixture to afford the compounds of formulae (28) and (29), dissolving these compounds in a mixed solvent system consisting of an organic solvent such as methanol or ethanol and an acidic aqueous solution such as conc. HCl, heating the solution to effect hydrolysis. The reaction for converting the compounds of formula (30) into the compound of formula (31) is carried out by dissolving the former compound in an acidic aqueous solution, adding hexamethylenetetramine, and heating the mixture, preferably dissolving said compound in an aqueous solution of acetic acid, heating the resulting solution under reflux, then adding an aqueous solution of hydrochloric acid, and heating the mixture under reflux. The compound of formula (31) is treated with a Grignard reagent, an organolithium compound and the like to afford the compound of formula (32) or (33) which, in turn, is dissolved in a solvent such as chloroform or dichloromethane; a Lewis acid such as boron trifluoride etherate is allowed to act on the solution to afford the compound of formula (34), which is optionally deprotected to yield the compound of formula (35).

In method H, the reaction for producing the compound of formula (37) from the compound of formula (36) [see Chem. Ber., 109, 1530–1548 (1976)] is performed by allowing a reducing agent such as sodium borohydride to act on the compound of formula (36). By selective protection and deprotection of either one of the two phenolic hydroxyl groups in the compound of formula (37), the compounds of formulae (38) and (39) and then the compound of formula (40) are produced. The compound of formula (40) is treated with an alkyl halide, an alkenyl halide or an alkynyl halide in a solvent such as tetrahydrofuran, N,N-dimethylformamide, N,N-dimethylacetamide or acetone in the presence of a base such as sodium hydride, potassium carbonate, sodium carbonate, sodium hydroxide or potassium hydroxide to afford the compound of formula (41), which is optionally deprotected to yield the compound of formula (42).

To produce the compounds of formulae (44) and (47), a halide such as 1,3-dibromopropane or 1-bromo-3-chloropropane is first allowed to act on the compound of formula (40) in a solvent such as tetrahydrofuran, N,N-dimethylformamide, N,N-dimethylacetamide or acetone in the presence of a base such as sodium hydride, potassium carbonate, sodium carbonate, sodium hydroxide or potassium hydroxide and, thereafter, a treatment is performed in the same way as employed to obtain the compound of formula (41) from the compound of formula (40), whereby the compounds of formulae (43) and (46) are obtained. These compounds are optionally deprotected to yield the compounds of formulae (44) and (47), respectively.

The following test cases (Nos. 1–6) are provided for the purpose of demonstrating that the compounds of the invention are superb as highly selective antioxidants.

The compounds under test were as follows:
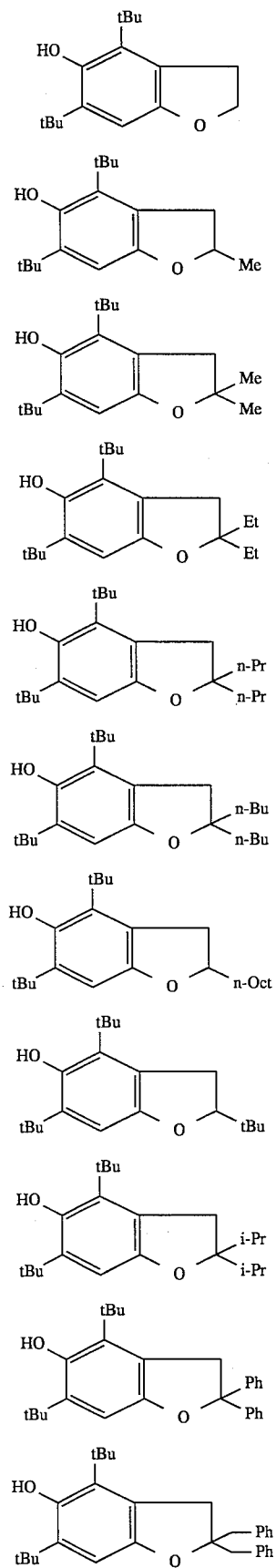
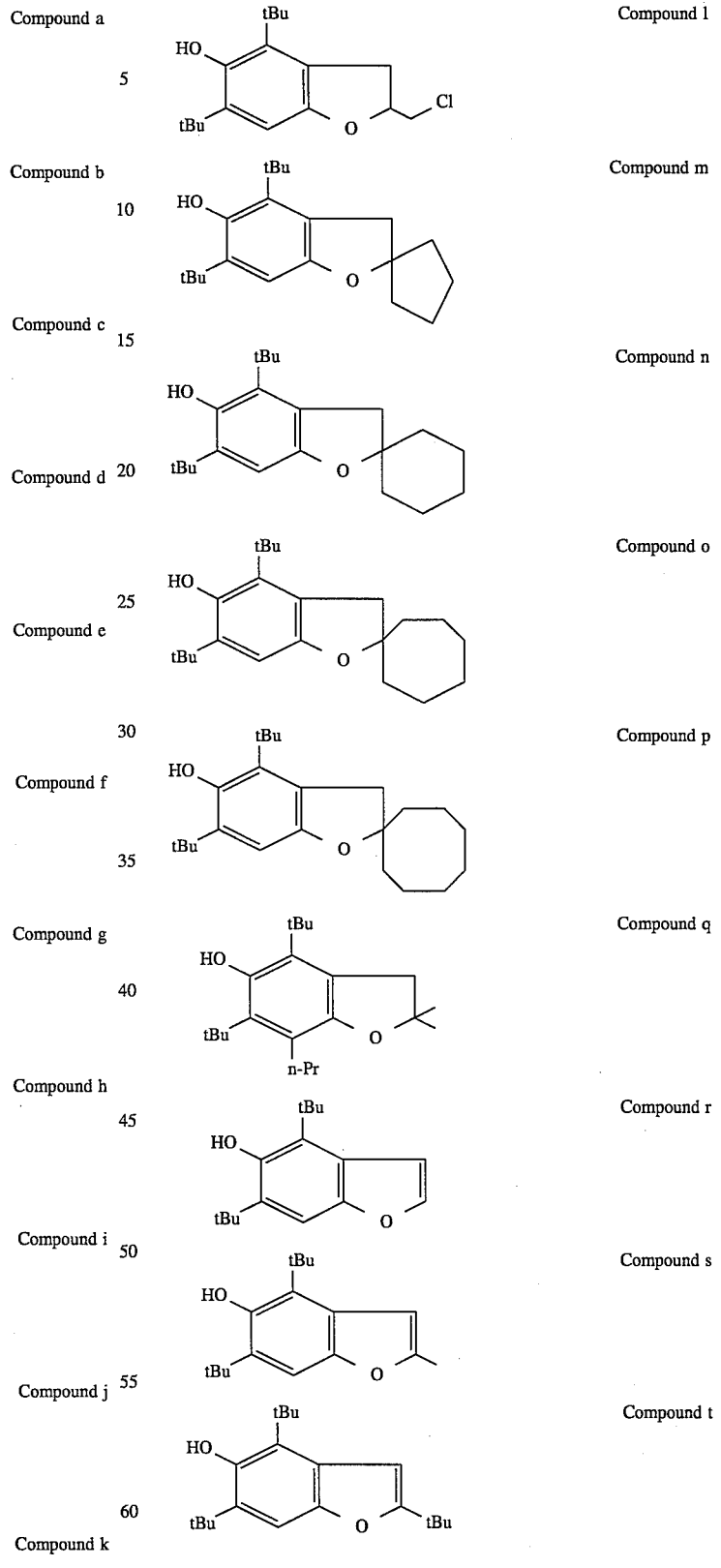

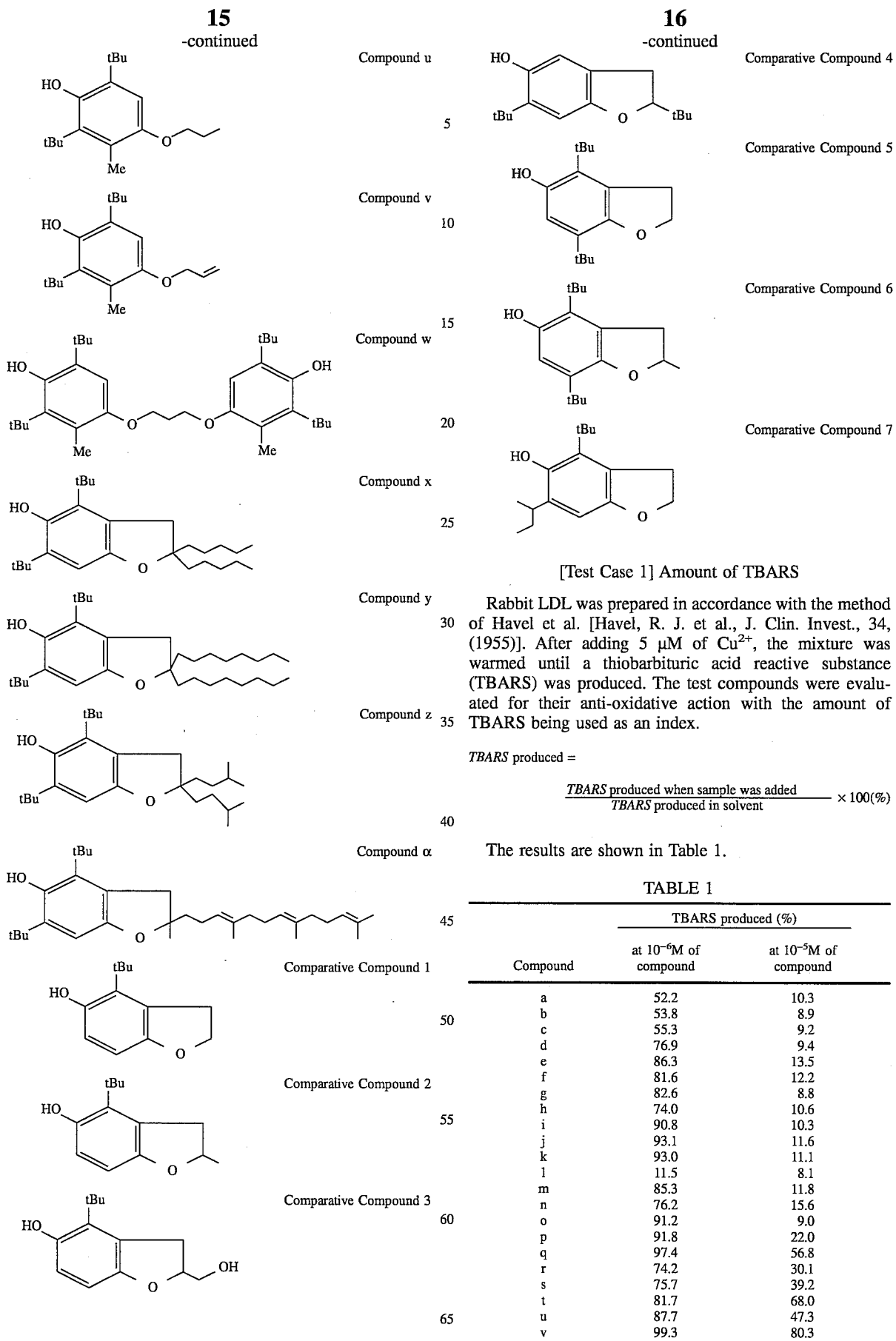

[Test Case 1] Amount of TBARS

Rabbit LDL was prepared in accordance with the method of Havel et al. [Havel, R. J. et al., J. Clin. Invest., 34, (1955)]. After adding 5 μM of $Cu^{2+}$, the mixture was warmed until a thiobarbituric acid reactive substance (TBARS) was produced. The test compounds were evaluated for their anti-oxidative action with the amount of TBARS being used as an index.

TBARS produced =

$$\frac{TBARS \text{ produced when sample was added}}{TBARS \text{ produced in solvent}} \times 100(\%)$$

The results are shown in Table 1.

TABLE 1

| Compound | TBARS produced (%) | |
|---|---|---|
| | at $10^{-6}$M of compound | at $10^{-5}$M of compound |
| a | 52.2 | 10.3 |
| b | 53.8 | 8.9 |
| c | 55.3 | 9.2 |
| d | 76.9 | 9.4 |
| e | 86.3 | 13.5 |
| f | 81.6 | 12.2 |
| g | 82.6 | 8.8 |
| h | 74.0 | 10.6 |
| i | 90.8 | 10.3 |
| j | 93.1 | 11.6 |
| k | 93.0 | 11.1 |
| l | 11.5 | 8.1 |
| m | 85.3 | 11.8 |
| n | 76.2 | 15.6 |
| o | 91.2 | 9.0 |
| p | 91.8 | 22.0 |
| q | 97.4 | 56.8 |
| r | 74.2 | 30.1 |
| s | 75.7 | 39.2 |
| t | 81.7 | 68.0 |
| u | 87.7 | 47.3 |
| v | 99.3 | 80.3 |

TABLE 1-continued

| Compound | TBARS produced (%) | |
|---|---|---|
| | at $10^{-6}$M of compound | at $10^{-5}$M of compound |
| w | 71.3 | 17.2 |
| x | 96.3 | 42.1 |
| y | 85.4 | 72.3 |
| z | 77.5 | 22.9 |

[Test Case 2] Effect Against Lipid Peroxidation by Autoxidation of Linoleic Acid Using a cypridina luciferin analog (2-methyl-6-(p-methoxyphenyl)-3,7-dihydroimidazo[1,2-a]pyrazin-3-one: MCLA) as a sensitizer for lipid peroxyl radicals, the test compounds were evaluated for their inhibitory effect against the generation of lipid peroxyl radicals by autoxidation of linoleic acid. A n-butanol solution (0.5 ml) containing MCLA (0.2 μM) and linoleic acid (10 mM) was used in a chemiluminescence measuring vial and the intensity of chemiluminescence due to the autoxidation of linoleic acid was measured in a thermostatic bath at 37° C.

$$MCLA = \frac{\text{Change in chemiluminescence intensity when sample was added}}{\text{Change in chemiluminescence intensity when solvent was added}} \times 100 (\%)$$

The results are shown in Table 2.

TABLE 2

| Compound | MCLA (%) | |
|---|---|---|
| | at $2 \times 10^{-5}$M of compound | at $2 \times 10^{-4}$M of compound |
| a | 21 | 2 |
| b | 24 | 2 |
| c | 18 | 1 |
| d | 36 | 2 |
| e | 23 | 1 |
| f | 39 | 3 |
| g | 31 | 2 |
| h | 33 | 3 |
| i | 72 | 5 |
| j | 66 | 10 |
| k | 55 | 4 |
| l | 24 | 3 |
| m | 24 | 1 |
| n | 23 | 1 |
| o | 26 | 1 |
| p | 44 | 3 |
| q | 11 | 1 |
| r | 97 | 68 |
| s | 78 | 36 |
| t | 93 | 41 |
| u | 83 | 30 |
| v | 101 | 15 |
| w | 35 | 2 |
| x | 13 | 2 |
| y | 16 | 1 |
| z | 10 | 2 |
| α | 13 | 4 |

[Test Case 3] Effect Against Fluorescence Generation of Rabbit LDL by AAPH

Using 2,2'-azobis(2-aminodipropane)hydrochloride (AAPH) which was a radical initiator for a lipid peroxidation that was not mediated by active oxygen [see Sato, K. et al., Arch. Biochem. Biophys., 279, 402 (1990)], the test compounds were evaluated for their inhibitory effect against fluorescence generation in rabbit LDL. Rabbit LDL was prepared in accordance with the method of Havel [Havel, R. J. et al., J. Clin. Invest., 34, 1345 (1955)]; after addition of AAPH (2 mM), the mixture was warmed at 37° C. for 24 h and LDL fraction was separated by gel-permeation chromatography. The fluorescence intensity of LDL fraction was measured by fluorometry at an excitation wavelength of 360 nm and at an emission wavelength of 430 nm.

$$AAPH = \frac{\text{Fluorescence intensity of LDL fraction when sample was added}}{\text{Fluorescence intensity of LDL fraction when solvent was added}} \times 100 (\%)$$

The results are shown in Table 3.

TABLE 3

| Compound | AAPH (%) at $10^{-4}$M of compound |
|---|---|
| a | 8 |
| b | 17 |
| c | 16 |
| d | 49 |
| e | 42 |
| f | 63 |
| g | 66 |
| h | 42 |
| i | 27 |
| j | 2 |
| k | 65 |
| m | 45 |
| n | 46 |
| o | 31 |
| p | 70 |
| t | 85 |
| u | 78 |
| v | 72 |
| w | 39 |
| x | 31 |
| y | 84 |

The results of Test Cases 1–3 obviously show that the tested compounds of the invention had an excellent antioxidative activity. The active oxygen induced by $Cu^{2+}$ in the TBARS experimental model in Test Case 1 is believed to be a direct radical initiator, so even a water-soluble active oxygen scavenger will be effective in that model. It should, however, be stressed that the tested compounds of the invention also proved to be effective in the AAPH using experimental model in Test Case 3 and, hence, it became clear that those compounds also suppressed the chain reaction for lipid peroxidation due to carbon-centered radicals which could not be inhibited by water-soluble active oxygen scavengers. This fact suggests that the compounds of the invention show effective anti-oxidative actions in LDL oxidation or lipid peroxidation.

[Test Case 4] Effect Against Linoleic Acid-MCLA System

The test compounds were evaluated for their inhibitory effect against lipid peroxidation due to the autoxidation of linoleic acid.

| | |
|---|---|
| Linoleic acid | 10 mM |
| MCLA | 2 µM |
| 1-Butanol solution | |

A reaction solution was prepared by mixing linoleic acid and MCLA (2-methyl-6-(p-methoxyphenyl)-3,7-dihydroimidazo[1,2-a]pyrazin-3-one) in 1-butanol and stored in ice until use. An amount of this reaction solution was sampled in a chemiluminescence measuring cell and, immediately thereafter, the intensity of chemiluminescence due to the autoxidation of linoleic acid was measured at 37° C. in a thermostatic bath. A normal chemiluminescence intensity measurement was conducted about 2–4 min later when the chemiluminescence substantially peaked. The results are shown in Table 4.

| Compound | 50% inhibition concentration (µM) |
|---|---|
| Comparison | |
| 1 | 62 |
| 2 | 54 |
| 3 | 54 |
| 4 | 42 |
| 5 | 41 |
| 6 | 19 |
| 7 | 7 |
| h | 9 |
| c | 7 |
| a | 7 |
| q | 5 |
| f | 8 |
| m | 7 |
| n | 9 |
| x | 5 |
| z | 6 |

The data in Table 4 show that the compounds having higher hydrophobicity in both ortho-positions of the phenolic hydroxyl group had a particularly high antioxidative activity.

[Test Case 5] Effect Against Xanthine Oxidase System (Superoxide Generating System)

The test compounds were evaluated under the following conditions for their effect in a reaction due to a xanthine oxidase (XOD)-hypoxanthine (HX) system in aqueous solution.

| | |
|---|---|
| Xanthine oxidase | 0.1 U/ml |
| Hypoxanthine | 400 µM |
| Luminol | 400 µM |
| Hepes buffer solution (pH 7.4) | 100 µM |

A reaction solution was prepared by mixing hypoxanthine and luminol in the Hepes buffer solution and stored in ice until use. After warming the reaction solution at 37° C. for about 10 min, the reaction was started by addition of the xanthine oxidase solution. A measurement was started right after the addition of xanthine oxidase and subsequent stirring; chemiluminescence intensity was normally measured right after the start of the reaction. In the experimental model, luminol-dependent chemiluminescence induced by superoxide generated by enzymatic reaction of xanthine oxidase was detected, thus enabling the measurement of the reactivity with superoxide. The results are shown in Table 5.

TABLE 5

| | Chemiluminescence intensity (% of control) | |
|---|---|---|
| Compound | at 20 µM of compound | at 200 µM of compound |
| Comparison | | |
| 1 | 23.9 | 6.3 |
| 2 | 32.7 | 3.2 |
| 5 | 21.9 | 8.2 |
| 6 | 31.9 | 24.0 |
| 7 | 55.8 | 17.5 |
| g | 88.6 | 104.8 |
| a | 41.8 | 26.1 |
| f | 91.0 | 102.4 |
| m | 83.1 | 89.8 |
| n | 100.3 | 104.9 |
| x | 84.5 | 85.6 |
| y | 94.2 | 110.2 |
| z | 99.2 | 107.5 |

[Test Case 6] Effect Against Lactoperoxidase System (Singlet Oxygen System)

The test compounds were evaluated under the following conditions for their effect against a lactoperoxidase reaction system.

| | |
|---|---|
| Lactoperoxidase | 10 µg/ml |
| $H_2O_2$ | 0.1% |
| NaBr | 20 mM |
| Luminol | 400 µM |
| Acetate buffer solution (pH 4.5) | 100 µM |

A reaction solution was prepared by mixing hydrogen peroxide, sodium bromide and luminol in the acetate buffer solution and stored in ice until use. After warming the reaction solution at 37° C. for about 10 min, the reaction was started by addition of the lactoperoxidase solution. A measurement was started right after the addition of lactoperoxidase and subsequent stirring; chemiluminescence intensity was measured right after the start of the reaction. In the experimental model, luminol-dependent chemiluminescence induced by singlet oxygen generated by enzymatic reaction of lactoperoxidase was detected, thus enabling the measurement of the reactivity with singlet oxygen.

TABLE 6

| | Chemiluminescence intensity (% of control) | |
|---|---|---|
| Compound | at 20 µM of compound | at 200 µM of compound |
| Comparison | | |
| 1 | 77.6 | 6.0 |
| 2 | 82.1 | 15.1 |
| 5 | 95.3 | 4.5 |
| 6 | 105.8 | 8.1 |
| 7 | 86.2 | 0.8 |
| g | 97.0 | 76.0 |
| a | 94.5 | 56.6 |
| q | 104.0 | 73.4 |

The results of Test Cases 5 and 6 obviously show that the compounds having high hydrophobicity in both ortho-positions of the phenolic hydroxyl group had low reactivity with so-called active oxygen species such as superoxides and singlet oxygen. It should particularly be mentioned that in the system for reaction with singlet oxygen, the test compounds of the invention which had two t-butyl groups in both ortho-positions of the phenolic hydroxyl group had a particularly low reactivity even compared with the compound (Comparative Compound 7) having a sec-butyl group in one of the two ortho-positions. This shows that compared to the conventional antioxidants described in Japanese Patent Public Disclosure (kokai) No. Hei 2-121975 and other prior patents, the compounds of the invention have a markedly high selectivity in the inhibitory action of lipid peroxidation, as evidenced by the fact that the compounds of the invention react in a particularly efficient manner with those radical species which are responsible for the lipid peroxidation while there are many free radical species in oxidation.

EXAMPLES

The following examples are provided for the purpose of further illustrating the invention but are in no way to be taken as limiting.

Example 1

Synthesis of
2,4,6-Tri-tert-Butyl-5-Hydroxybenzofuran
(Compound t) and
4,6-Di-tert-Butyl-5-Hydroxybenzofuran (Compound r)

Methanesulfonic acid (140 ml) was added dropwise, under ice cooling, to a solution consisting of 4-tert-butyl-5-hydroxybenzofuran [J. Org. Chem., 53, 4135 (1988); 35 g, 0.18 mol], tert-butyl alcohol (70 g, 0.84 mol) and chloroform (50 ml). After stirring at 0° C. for 20 min, the mixture was poured into ice water. Subsequently, the mixture was neutralized with an aqueous solution of 1N sodium hydroxide and subjected to extraction with ethyl acetate. The extracted layer was washed with a saturated aqueous solution of sodium hydrogen carbonate, dried over anhydrous magnesium sulfate, and concentrated. The concentrate was purified by silica gel chromatography (n-hexane) to afford 2,4,6-tri-tert-butyl-5-hydroxybenzofuran [10.87 g (yield, 20%)]. Also obtained, though in low yield, was 4,6-di-tert-butyl-5-hydroxybenzofuran.

2,4,6-Tri-tert-butyl-5-hydroxybenzofuran m.p. 115.5° C. (fine-grained, pale yellow crystal) Mass 302($M^+$), 287, 57

$^1$H NMR (60 MHz, CDCl$_3$) δ ppm 1.33(s,9H), 1.47(s, 9H), 1.62(s,9H), 5.06(s,1H), 6.58(s,1H), 7.29(s,1H)

IR (cm$^{-1}$) 3641, 2969

4,6-Di-tert-butyl-5-hydroxybenzofuran m.p. 60.3° C. (fine-grained, pale yellow crystal) Mass 246($M^+$), 231, 57

$^1$H NMR (60 MHz, CDCl$_3$) δ ppm 1.49(s,9H), 1.62(s, 9H), 5.11(s,1H), 7.02(d,1H,J=2.4 Hz), 7.35(s,1H), 7.43(d, 1H,J=2.4 Hz)

IR (cm$^{-1}$) 3648, 2960

Example 2

Synthesis of
2,4,6-Tri-tert-Butyl-5-Hydroxy-2,3-Dihydrobenzofuran
(Compound h)

Triethylsilane (76 ml) was added to 2,4,6-tri-tert-butyl-5-hydroxybenzofuran (24.7 g, 82 mmol) and trifluoroacetic acid (38 ml) was added dropwise to the mixture under ice cooling. The mixture was stirred first at 0° C. for 15 min, then at room temperature for 15 min before it was poured into ice water. The mixture was neutralized with an aqueous solution of 1N sodium hydroxide and subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (chloroform) to afford 2,4,6-tri-tert-butyl-5-hydroxy-2,3-dihydrobenzofuran [19.0 g (yield, 76%)].

m.p 91.4° C. (white needle; recrystallized from n-hexane) Mass 304($M^+$), 289, 57

$^1$H NMR (60 MHz, CDCl$_3$) δ ppm 0.97(s,9H), 1.40(s, 9H), 1.50(s,9H), 3.22(dd,2H,J=8.0 Hz, J=11.0 Hz), 4.24(dd, 1H,J=8.0 Hz,J=11.0 Hz), 4.66(s,1H), 6.67(s,1H)

IR (cm$^{-1}$) 3669, 2973

Example 3

Synthesis of
4,6-Di-tert-Butyl-5-Hydroxy-2,3-Dihydrobenzofuran
(Compound a)

Methanesulfonic acid (10 ml) was added dropwise, under ice cooling, to a solution consisting of 4-tert-butyl-5-hydroxy-2,3-dihydrobenzofuran [J. Org. Chem., 53, 4135 (1988); 2.84 g, 15 mmol], tert-butyl alcohol (10 g, 120 mmol) and chloroform (20 ml). After stirring at 0° C. for 15 min, the mixture was poured into ice water. The mixture was neutralized with an aqueous solution of 1N sodium hydroxide and subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (n-hexane) to afford 4,6-di-tert-butyl-5-hydroxy-2,3-dihydrobenzofuran [210 mg (yield, 6%)].

m.p. 113.4° C. (colorless, fine-grained crystal; recrystallized from n-hexane) Mass 248($M^+$), 233, 191, 57

$^1$H NMR (60 MHz, CDCl$_3$) δ ppm 1.42(s,9H), 1.50(s, 9H), 3.40(t,2H,J=8.0 Hz), 4.37(t,2H,J=8.0 Hz), 4.72(s,1H), 6.68(s,1H)

IR (cm$^{-1}$) 3623, 2969

Reference Example 1

Synthesis of 5-Benzyloxy-4-tert-Butylbenzofuran 4-tert-butyl-5-hydroxybenzofuran [J. Org. Chem., 53, 4135 (1988); 40 g, 0.21 mol], benzyl bromide (43 g, 0.25 mol) and potassium carbonate (28.8 g, 0.21 mol) were dissolved in N,N-dimethylformamide (200 ml) and the solution was stirred at room temperature for 24 h. After distilling off the N,N-dimethylformamide under vacuum, water was added to the residue and the mixture was subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (10% ethyl acetate in n-hexane) to afford 5-benzyloxy-4-tert-butylbenzofuran [49.1 g (yield, 83%)]. Mass 280(M+), 224, 189, 161, 91

$^1$H NMR (60 MHz, CDCl$_3$) δ ppm 1.57(s,9H), 5.06(s, 2H), 6.86–7.43(m,9H)

Reference Example 2

Synthesis of
5-Benzyloxy-4-tert-Butyl-2-Formylbenzofuran

Phosphorus oxychloride (26.2 ml, 0.29 mol) was added dropwise to N,N-dimethylformamide (17 ml, 0.22 mol) under ice cooling; subsequently, a solution of 5-benzyloxy-4-tert-butylbenzofuran (40 g, 0.14 mol) in N,N-dimethylformamide (10 ml) was added dropwise. The mixture was stirred first at room temperature for 20 min, then under heating at 80° C. for 2 h. After cooling, the reaction mixture was poured into water and extracted with ethyl acetate. The extracted layer was washed with a saturated aqueous solution of sodium hydrogen carbonate and water, dried over anhydrous magnesium sulfate and concentrated. The concentrate was purified by silica gel chromatography (10% ethyl acetate in n-hexane) to afford 5-benzyloxy-4-tert-butyl-2-formylbenzofuran [16.2 g (yield, 36%)].

m.p. 135.7° C. Mass 308(M+), 91

$^1$H NMR (60 MHz, CDCl$_3$) δ ppm 1.58(s,9H), 5.10(s, 2H), 7.20–7.48(m,7H), 7.92(s,1H), 9.76(s,1H)

Reference Example 3

Synthesis of
4-tert-Butyl-5-Hydroxy-2-Hydroxymethyl-2,3-Dihydrobenzofuran

5-Benzyloxy-4-tert-butyl-2-formylbenzofuran (5.0 g, 16 mmol) was dissolved in a 25:1 mixed solution (260 ml) of ethyl acetate and acetic acid. After adding 10% Pd on carbon (5.0 g), the solution was stirred under a hydrogen atmosphere for 48 h. After filtering off the Pd on carbon, the filtrate was washed with a saturated aqueous solution of sodium hydrogen carbonate, dried over anhydrous magnesium sulfate and concentrated. The concentrate was subjected to silica gel chromatography and eluted with a solvent system consisting of a 4:1 mixture of hexane and ethyl acetate to afford 4-tert-butyl-5-hydroxy-2-hydroxymethyl-2,3-dihydrobenzofuran [3.1 g (yield, 87%)] as a colorless oil. Mass 222(M+), 207, 57

$^1$H NMR (60 MHz, CDCl$_3$) δ ppm 1.44(s,9H), 2.95(bs, 1H), 3.09–3.91(m,4H), 4.51–4.93(m,1H), 6.04(bs,1H), 6.46(s,2H)

Reference Example 4

Synthesis of
4-tert-Butyl-2-Chloromethyl-5-Hydroxy-2,3-Dihydrobenzofuran

Pyridine (180 mg, 2.2 mmol) was added to a solution of 4-tert-butyl-5-hydroxy-2-hydroxymethyl-2,3-dihydrobenzofuran (430 mg, 1.9 mmol) in benzene (15 ml) and, subsequently, thionyl chloride (310 mg, 2.6 mmol) was added dropwise under ice cooling. After being allowed to warm to room temperature, the mixture was heated under reflux for 24 h. After cooling, water was added and the solution was extracted with ethyl acetate. The organic layer was washed with a saturated aqueous solution of sodium hydrogen carbonate and water, then dried over anhydrous magnesium sulfate and concentrated. The concentrate was purified by silica gel chromatography (chloroform) to afford 4-tert-butyl-2-chloromethyl-5-hydroxy-2,3-dihydrobenzofuran [280 mg (yield, 61%)] as a colorless oil. Mass 242(M+2), 240(M+), 227, 225, 57

$^1$H NMR (60 MHz, CDCl$_3$) δ ppm 1.45(s,9H), 3.07–3.83(m,4H), 4.56–5.02(m,1H), 5.39(s,1H), 6.47(s,2H)

Example 4

Synthesis of
4,6-tert-Butyl-2-Chloromethyl-5-Hydroxy-2,3-Dihydrobenzofuran (Compound 1)

Methanesulfonic acid (1.2 ml) was added dropwise to a solution of 4-tert-butyl-2-chloromethyl-5-hydroxy-2,3-dihydrobenzofuran (280 mg, 1.2 mmol) and tert-butyl alcohol (500 mg, 6.0 mmol) in chloroform (2 ml) under ice cooling. After stirring at 0° C. for 15 min, the mixture was poured into ice water. The mixture was then neutralized with an aqueous solution of 1N sodium hydroxide and subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (n-hexane) to afford 4,6-tert-butyl-2-chloromethyl-5-hydroxy-2,3-dihydrobenzofuran (10 mg) as a pale yellow oil. Mass 298(M+2), 296(M+), 283, 281, 57

$^1$H NMR (60 MHz, CDCl$_3$) δ ppm 1.41(s,9H), 1.50(s, 9H), 3.19–3.91(m,4H), 4.58–5.03(m,1H), 4.76(s,1H), 6.69(s,1H)

IR (cm$^{-1}$) 3460, 2960

Reference Example 5

Synthesis of
5-Benzyloxy-4-tert-Butyl-2-(1-octenyl)benzofuran

A pentane solution (2.6 ml, 4.2 mmol) of 1.6M n-butyllithium was added dropwise to a solution of n-heptyltriphenylphosphonium bromide (1.84 g, 4.2 mmol) in tetrahydrofuran (10 ml) under a nitrogen atmosphere. After stirring the mixture at room temperature for 30 min, a solution of 5-benzyloxy-4-tert-butyl-2-formylbenzofuran (1.0 g, 3.2 mmol) in tetrahydrofuran (10 ml) was added dropwise. Subsequently, the mixture was stirred at room temperature for 30 min, poured into ice water and subjected to extraction with ethyl acetate. The organic layer was washed with a saturated aqueous solution of sodium hydrogen carbonate and water, then dried over anhydrous magnesium sulfate and concentrated. The concentrate was purified by silica gel chromatography (chloroform) to afford 5-benzyloxy-4-tert-butyl-2-(1-octenyl)benzofuran [1.14 g (yield, 91%)]. Mass 392(M+), 301, 277, 167, 91, 57

$^1$H NMR (60 MHz, CDCl$_3$) δ ppm 0.89(t,3H), 1.13–1.72(m,8H), 1.56(s,9H), 1.93–2.62(m,2H), 5.03(s,2H), 6.02–6.40(m,2H), 6.78–7.46(m,8H)

Reference Example 6

Synthesis of
4-tert-Butyl-5-Hydroxy-2-Octylbenzofuran

10% Palladium on carbon (1.1 g) was added to a solution of 5-benzoxy-4-tert-butyl-2-(1-octenyl)benzofuran (1.1 g, 2.9 mmol) in acetic acid (50 ml), and the mixture was stirred for 36 h under a hydrogen atmosphere. After filtering off the Pd on carbon, the solvent was distilled off with an evaporator. The concentrate was purified by silica gel chromatography (chloroform) to afford 4-tert-butyl-5-hydroxy-2-octylbenzofuran [600 mg (yield, 69%)] as a pale yellow oil. Mass 302($M^+$), 287, 57

$^1$H NMR (60 MHz, CDCl$_3$) δ ppm 0.87(t,3H), 1.06–1.83(m,12H), 1.57(s,9H), 2.70(t,2H), 4.67(s,1H), 6.50(d,1H,J=8.4 Hz), 6.68(s,1H), 7.07(d,1H,J=8.4 Hz)

Reference Example 7

Synthesis of 4-tert-Butyl-5-Hydroxy-2-Octyl-2,3-Dihydrobenzofuran

Triethylsilane (2.8 ml) was added to 4-tert-butyl-5-hydroxy-2-octylbenzofuran (300 mg, 1.0 mmol) and, then, trifluoroacetic acid (1.4 ml) was added dropwise under ice cooling. The mixture was stirred first at 0° C. for 15 min, then at room temperature for 1 h. Thereafter, the mixture was poured into ice water and subjected to extraction with ethyl acetate. The organic layer was washed with a saturated aqueous solution of sodium hydrogen carbonate, dried over anhydrous magnesium sulfate and concentrated. The concentrate was purified by silica gel chromatography (chloroform) to afford 4-tert-butyl-5-hydroxy-2-octyl-2,3-dihydrobenzofuran [252 mg (yield, 83%)] as a colorless oil. Mass 304($M^+$), 289, 137, 57

$^1$H NMR (60 MHz, CDCl$_3$) δ ppm 0.87(t,3H), 1.12–1.75(m,14H), 1.44(s,9H), 2.75–3.70(m,2H), 4.09–4.68(m,1H), 4.45(s,1H), 6.42(s,2H)

Example 5

Synthesis of 4,6-Di-tert-Butyl-5-Hydroxy-2-Octyl-2,3-Dihydrobenzofuran (Compound g)

Methanesulfonic acid (1.5 ml) was added dropwise, under ice cooling, to a solution consisting of 4-di-tert-butyl-5-hydroxy-2-octyl-2,3-dihydrobenzofuran (510 mg 1.7 mmol), tert-butyl alcohol (850 mg, 10.0 mmol) and chloroform (2 ml). After stirring at 0° C. for 15 min, the mixture was poured into ice water. The mixture was then neutralized with an aqueous solution of 1N sodium hydroxide and subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (n-hexane) to afford 4,6-di-tert-butyl-5-hydroxy-2-octyl-2,3-dihydrobenzofuran (83 mg) as a pale yellow oil. Mass 360($M^+$), 345, 57

$^1$H NMR (60 MHz, CDCl$_3$) δ ppm 0.90(t,3H), 1.12–1.95(m,14H), 1.42(s,9H), 1.50(s,9H), 2.80–3.70(m, 2H), 4.35–4.80(m,1H), 4.67(s,1H), 6.63(s,1H)

IR (cm$^{-1}$) 3624, 2935

Reference Example 8

Synthesis of 4-Acetoxy-3,5-Di-tert-Butylanisole

4-Hydroxy-3,5-di-tert-butylanisole (23.6 g) was dissolved in acetic anhydride (150 ml). Following the addition of conc. sulfuric acid (0.5 ml), the mixture was stirred at 70° C. for 2 h. The reaction mixture was concentrated under reduced pressure and a saturated aqueous solution of sodium hydrogen carbonate was added to the concentrate, followed by extraction with ethyl acetate. The extracted layer was dried over anhydrous magnesium acetate and concentrated. The precipitating solid was recrystallized from methanol-water (2:1) to afford 4-acetoxy-3,5-di-tert-butylanisole [24.5 g (yield, 88%)] as a white solid.

m.p. 96.6° C.

$^1$H NMR (60 MHz, CDCl$_3$) δ ppm 1.06(s,18H), 2.02(s, 3H), 3.47(s,3H), 6.53(s,2H) Mass 278($M^+$)

Reference Example 9

Synthesis of 4-Acetoxy-3,5-Di-tert-Butylphenol

4-Acetoxy-3,5-di-tert-butylanisole (0.50 g) was dissolved in dichloromethane (2 ml). After cooling with ice, trimethylsilyl iodide (0.31 ml) was added dropwise. The mixture was allowed to warm slowly to room temperature and stirred for 2 days; thereafter, a saturated aqueous solution of sodium hydrogen carbonate was added to the reaction mixture. The mixture was subjected to extraction with diethyl ether and the organic layer was washed with saturated brine, dried over anhydrous magnesium sulfate and concentrated. The residue was purified by silica gel chromatography (15% ethyl acetate in n-hexane) to afford 4-acetoxy-3,5-di-tert-butylphenol [0.38 g (yield, 80%)] as a white solid.

m.p. 156.9° C.

$^1$H NMR (60 MHz, CDCl$_3$) δ ppm 1.27(s,18H), 2.27(s, 3H), 5.22(brs,1H), 6.67(s,2H) Mass 222($M^+$)

Reference Example 9

Synthesis of 4-Acetoxy-3,5-Di-tert-Butyl-1-(2-Methyl-2-Propenyloxy)benzene

60% Oily sodium hydride (0.18 g) was suspended in N,N-dimethylformamide (10 ml). A solution of 4-acetoxy-3,5-di-tert-butylphenol (1 g) in N,N-dimethylformamide (5 ml) was added dropwise to the suspension under ice cooling and the mixture was stirred for 30 min. Subsequently, the reaction mixture was allowed to warm to room temperature and 3-chloro-2-methyl-1-propene (0.45 ml) was added dropwise. After stirring at room temperature for 2 h, a saturated aqueous solution of ammonium chloride (15 ml) was added to the reaction mixture. The mixture was subjected to extraction with diethyl ether and the organic layer was washed with water and saturated brine, dried over anhydrous magnesium sulfate and concentrated. The concentrate was purified by silica gel chromatography (10% ethyl acetate in n-hexane) to afford 4-acetoxy-3,5-di-tert-butyl-1-(2-methyl-2-propenyloxy)benzene [1.08 g (yield, 90%)] as a colorless liquid.

$^1$H NMR (60 MHz, CDCl$_3$) δ ppm 1.30(s,18H), 1.83(s, 3H), 2.30(s,3H), 4.37(brd,J=6.6 Hz,2H), 6.83(s,2H) Mass 318($M^+$)

Example 6

Synthesis of 5-Acetoxy-4,6-Di-tert-Butyl-2,2-Dimethyl-2,3-Dihydrobenzofuran

4-Acetoxy-3,5-di-tert-butyl-1-(2-methyl-2-propenyloxy)benzene (2.22 g) was dissolved in N,N-dimethylaniline (8 ml) and the solution was refluxed under a nitrogen atmosphere for 36 h. After cooling to room temperature, the reaction solution was concentrated under reduced pressure and, after addition of 1N HCl (5 ml) and diethyl ether (10 ml), stirring was continued for 15 min. The organic layer was separated and the aqueous layer was subjected to extraction with diethyl ether. The combined extracts were washed with saturated brine, dried over anhydrous magnesium sulfate and concentrated. The concentrate was purified by silica gel chromatography (5% ethyl acetate in n-hexane) to afford 5-acetoxy-4,6-di-tert-butyl-2,2-dimethyl-2,3-dihydrobenzofuran [1.19 g (yield, 54%)] as a white solid.

m.p. 97.7° C.

$^1$H NMR (60 MHz, CDCl$_3$) δ ppm 1.16–1.60(m,24H), 2.25(s,3H), 3.18(s,2H), 6.63(s,1H) Mass 318(M$^+$)

Example 7

Synthesis of 5-Hydroxy-4,6-Di-tert-Butyl-2,2-Dimethyl-2,3-Dihydrobenzofuran (Compound c)

Lithium aluminum hydride (0.10 g) was suspended in tetrahydrofuran (5 ml) under a nitrogen atmosphere. A solution of 5-acetoxy-4,6-di-tert-butyl-2,2-dimethyl-2,3-dihydrobenzofuran (0.86 g) in tetrahydrofuran (6 ml) was added dropwise to the suspension and the mixture was refluxed for 4 h. After cooling the mixture to room temperature, water was added dropwise to quench the excess lithium aluminum hydride. After adding 1N aqueous sodium hydroxide (5 ml), the mixture was subjected to extraction with diethyl ether. The organic layer was washed with saturated brine, dried over anhydrous magnesium sulfate and concentrated. The concentrate was purified by silica gel chromatography (5% ethyl acetate in n-hexane) to afford 5-acetoxy-4,6-di-tert-butyl-2,2-dimethyl-2,3-dihydrobenzofuran [0.62 g (yield, 83%)] as a white solid.

m.p. 139.6° C.

$^1$H NMR (60 MHz, CDCl$_3$) δ ppm 1.42(s,18H), 1.50(s, 6H), 3.25(s,2H), 4.70(s,1H), 6.66(s,1H) Mass 276(M$^+$)

IR (cm$^{-1}$) 3632, 2964, 1404, 1386, 1134

Reference Example 10

Synthesis of 4-Acetoxy-3,5-Di-tert-Butyl-1-(2-Propenyloxy)benzene

4-Acetoxy-3,5-di-tert-butylphenol (10 g) and potassium carbonate (15.6 g) were dissolved in acetone (300 ml). After addition of 3-bromo-1-propene (6.55 ml), the mixture was refluxed for 24 h. The reaction mixture was concentrated under reduced pressure and water was added to the concentrate. The mixture was subjected to extraction with diethyl ether and the organic layer was washed with water and saturated brine, then dried over anhydrous magnesium sulfate and concentrated. The concentrate was purified by silica gel chromatography (10% ethyl acetate in n-hexane) to afford 4-acetoxy-3,5-di-tert-butyl-1-(2-propenyloxy)benzene (11 g) as a colorless liquid in a quantitative yield.

$^1$H NMR (60 MHz, CDCl$_3$) δ ppm 1.30(s,18H), 2.27(s, 3H), 4.47(d,J=5.0 Hz,2H), 5.05–5.57(brm,2H), 5.68–6.37(brm,1H), 6.81(s,2H) Mass 304(M$^+$)

Reference Example 11

Synthesis of 4-Acetoxy-3,5-Di-tert-Butyl-2-(2-Propenyloxy)phenol

4-Acetoxy-3,5-di-tert-butyl-1-(2-propenyloxy)benzene (11.0 g) was dissolved in N,N-dimethylaniline (50 ml) and the solution was refluxed for 18 h under a nitrogen atmosphere. After cooling to room temperature, the reaction solution was concentrated under reduced pressure and purified by silica gel chromatography (15% ethyl acetate in n-hexane) to afford 4-acetoxy-3,5-di-tert-butyl-2-(2-propenyl)phenol [8.84 g (yield, 77%)] as a white solid.

m.p. 103.6° C.

$^1$H NMR (60 MHz, CDCl$_3$) δ ppm 1.30(s,9H), 1.42(s, 9H), 2.28(s,3H), 3.52–3.84(m,2H), 4.88–5.42(m,3H), 5.68–6.45(m,1H), 6.79(s,1H) Mass 304(M$^+$)

Reference Example 12

4-Acetoxy-3,5-Di-tert-Butyl-1-(2-Methyl-2-ProPenyloxy)-2-Propylbenzene

4-Acetoxy-3,5-tert-butyl-2-(2-propenyl)phenol (0.90 g) was dissolved in ethyl acetate (15 ml). After adding 10% Pd on carbon (0.005 g), the solution was stirred vigorously under a hydrogen atmosphere for 18 h. The Pd on carbon was filtered off and the filtrate was concentrate. The concentrate was dissolved in N,N-dimethylformamide (5 ml) and the solution was added dropwise to a suspension of 60% oily sodium hydride (0.14 g) in N,N-dimethylformamide (7 ml) under ice cooling and the mixture was stirred for 30 min. Subsequently, the reaction mixture was allowed to warm to room temperature and 3-chloro-2-methyl-1-propene (0.35 ml) was added dropwise. After stirring at room temperature for 2 h, water (15 ml) was added to the reaction mixture. The mixture was subjected to extraction with diethyl ether and the organic layer was washed with water and saturated brine, then dried over anhydrous magnesium sulfate and concentrated. The concentrate was purified by silica gel chromatography (5% ethyl acetate in n-hexane) to afford 4-acetoxy-3,5-di-tert-butyl-1-(2-methyl-2-propenyloxy)-2-propylbenzene [0.82 g (yield, 77%)] as a colorless liquid.

$^1$H NMR (60 MHz, CDCl$_3$) δ ppm 0.70–1.72(m,23H), 1.86(s,3H), 2.28(s,3H), 2.65–3.12(m,2H), 4.39(s,2H), 5.06(d,J=9.0 Hz,2H), 6.82(s,1H) Mass 360(M$^+$)

Example 8

Synthesis of 5-Acetoxy-4,6-Di-tert-Butyl-2,2-Dimethyl-7-Propyl-2,3-Dihydrobenzofuran 4-Acetoxy-3,5-di-tert-butyl-1-(2-methyl-2-propenyloxy)-2-propylbenzene (0.82 g) was dissolved in N,N-dimethylaniline (8 ml) and the solution was refluxed for 18 h under a nitrogen atmosphere. After cooling to room temperature, the reaction solution was concentrated under reduced pressure and 1N HCl (5 ml) and diethyl ether (10 ml) were added to the concentrate, followed by stirring for 15 min. The organic layer was separated and the aqueous layer was subjected to extraction with diethyl ether. The combined extracts were washed with saturated brine, dried over anhydrous magnesium sulfate and concentrated. The concentrate was purified by silica gel chromatography (5% ethyl acetate in n-hexane) to afford 5-acetoxy-4,6-di-tert-butyl-2,2-dimethyl-7-propyl-2,3-dihydrobenzofuran [0.60 g (yield, 73%)] as a pale yellow solid.

m.p. 106.0° C.

$^1$H NMR (60 MHz, CDCl$_3$) δ ppm 0.55–2.08(m,29H), 2.23(s,3H), 2.72(t,J=7.0 Hz,2H), 3.17(s,2H) Mass 360(M$^+$)

Example 9

Synthesis of 5-Hydroxy-4,6-Di-tert-Butyl-2,2-Dimethyl-7-Propyl-2,3-Dihydrobenzofuran (Compound g)

Lithium aluminum hydride (0.08 g) was suspended in tetrahydrofuran (5 ml) under a nitrogen atmosphere. A solution of 5-acetoxy-4,6-di-tert-butyl-2,2-dimethyl-7-propyl-2,3-dihydrobenzofuran (0.60 g) in tetrahydrofuran (5 ml) was added dropwise to the suspension and the mixture was refluxed for 4 h. After cooling the reaction mixture to room temperature, water was added dropwise to quench the excess lithium aluminum hydride. Thereafter 1N aqueous sodium hydroxide (5 ml) was added and the mixture was subjected to extraction with diethyl ether, washed with saturated brine, dried over anhydrous magnesium sulfate and concentrated. The concentrate was purified by silica gel chromatography (5% ethyl acetate in n-hexane) to afford 5-hydroxy-4,6-di-tert-butyl-2,2-dimethyl-7-propyl-2,3-dihydrobenzofuran [0.17 g (yield, 32%)] as a pale yellow solid.

m.p. 90.3° C. (dec.)

$^1$H NMR (60 MHz, CDCl$_3$) δ ppm 0.70–2.10(m,29H), 2.57–3.10(m,4H), 3.23(s,2H), 4.83(s,1H) Mass 318(M$^+$)

IR (cm$^{-1}$) 3648, 2952, 2868, 1368, 1366, 1290, 1260, 1152, 924.

Example 10

Synthesis of 4,6-Di-tert-Butyl-5-Hydroxy-2-Methyl-2,3-Dihydrobenzofuran (Compound b)

4-Acetoxy-3,5-di-tert-butyl-2-(2-propenyl)phenol (1.0 g, 3.3 mmol) was dissolved in dichloromethane (10 ml) and BF$_3$ etherate (0.7 ml) was added dropwise to the solution under a nitrogen atmosphere. The mixture was stirred for 24 h at room temperature and, thereafter, water was added and the mixture was extracted with ethyl acetate. The extracted layer was washed with a saturated aqueous solution of sodium hydrogen carbonate, dried over anhydrous magnesium sulfate and concentrated. The concentrate was dissolved in tetrahydrofuran (5 ml) and the solution was added dropwise to a suspension of lithium aluminum hydride (76 mg) in tetrahydrofuran (5 ml) that had been prepared under a nitrogen atmosphere. After refluxing for 3 h, the reaction mixture was cooled to room temperature and water was added dropwise. Following the addition of 1N aqueous sodium hydroxide, the mixture was subjected to extraction with diethyl ether. The organic layer was dried over anhydrous magnesium sulfate and concentrated. The concentrate was purified by silica gel chromatography (10% ethyl acetate in n-hexane) to afford 4,6-di-tert-butyl-5-hydroxy-2-methyl-2,3-dihydrobenzofuran [450 mg (yield, 52%)].

m.p. 86.8° C. Mass 262(M$^+$), 247, 205, 57

$^1$H NMR (60 MHz, CDCl$_3$) δ ppm 1.40(d,3H), 1.42(s, 9H), 1.50(s,9H), 2.80–3.80(m,2H), 4.42–4.92(m,1H), 4.71(s,1H), 6.70(s,1H )

IR (cm$^{-1}$) 3616, 2960

Reference Example 13

Synthesis of 4-Acetoxy-3,5-Di-tert-Butyl-2-(Chloroacetylaminomethyl)phenol and 6-Acetoxy-5,7-Di-tert-Butyl-3-(2-Chloroacetyl)-2,3-Dihydro-1,3,4H-Benzoxazine 4-Acetoxy-3,5-di-tert-butylphenol (29 g, 0.11 mol) was dissolved in a 9:1 mixed solution (200 ml) of acetic acid and sulfuric acid. Following addition of N-hydroxy-methyl-2-chloroacetamide (34 g, 0.28 mol), the mixture was stirred at room temperature for 48 h. Subsequently, the reaction mixture was poured into water, neutralized with 1N aqueous sodium hydroxide and subjected to extraction with ethyl acetate. The organic layer was dried over anhydrous magnesium sulfate and concentrated. The concentrate was used in the subsequent reaction without further purification. When part of the concentrate was subjected to silica gel chromatography and eluted with a solvent system consisting of a 4:1 mixture of hexane and ethyl acetate, the following two products were obtained: 4-acetoxy-3,5-di-tert-butyl-2-(chloroacetylaminomethyl)phenol and 6-acetoxy-5,7-di-tert-butyl-3-(2-chloroacetyl)-2,3-dihydro-1,3,4H-benzoxazine.

4-Acetoxy-3,5-Di-tert-Butyl-2-(Chloroacetylaminomethyl)phenol (colorless oil) Mass 369(M$^+$), 327, 234, 57

$^1$H NMR (60 MHz, CDCl$_3$) δ ppm 1.30(s,9H), 1.43(s, 9H), 2.28(s,3H), 4.00(s,2H), 4.73(d,2H,J=6.0 Hz), 6.88(s, 1H), 7.54 (t,1H,J=6.0 Hz)

6-Acetoxy-5,7-Di-tert-Butyl-3-(2-Chloroacetyl)-2,3-Dihydro-1,3,4H-Benzoxazine (colorless oil) Mass 381(M$^+$), 339, 304, 57

$^1$H NMR (60 MHz, CDCl$_3$) δ ppm 1.30(s,9H), 1.47(s, 9H), 2.30(s,3H), 4.17(s,2H), 5.00(s,2H), 5.33(s,2H), 6.83(s, 1H)

Reference Example 14

Synthesis of 4-Acetoxy-2-Aminomethyl-3,5-Di-tert-Butylphenol

The concentrate obtained in Reference Example 13 was dissolved in a 10:3 mixed solution (550 ml) of ethanol and conc. HCl and the solution was heated under reflux for 2 h. After cooling, the reaction solution was poured into water and the mixture was neutralized with 1N aqueous sodium hydroxide, followed by extraction with ethyl acetate. The organic layer was dried over anhydrous magnesium sulfate and concentrated. The concentrate was used in the subsequent reaction without further purification. When part of the concentrate was subjected to silica gel chromatography and eluted solvent system consisting of a 4:1 mixture of chloroform and methanol, 4-acetoxy-2-aminomethyl-3,5-di-tert-butylphenol was obtained as a main product.

4-Acetoxy-2-Aminomethyl-3,5-Di-tert-Butylphenol (colorless oil) Mass 293(M$^+$), 234, 191, 57

$^1$H NMR (60 MHz, CDCl$_3$) δ ppm 1.27(s,9H), 1.37(s, 9H), 2.25(s,3H), 4.22(s,2H), 5.18(bs,3H), 6.85(s,1H)

Example 11

Synthesis of 5-Acetoxy-4,6-Di-tert-Butyl-2-Hydroxybenzaldehyde

The concentrate obtained in Reference Example 14 was dissolved in a 11:3 mixed solution (636 ml) of acetic acid and water and, after addition of hexamethylenetetramine (19.3 g, 0.11 mol), the mixture was heated under reflux for 4 h. Subsequently, 4.5N HCl (85 ml) was added and the mixture was heated under reflux for 20 min. After cooling, the reaction mixture was poured into water, neutralized with 1N aqueous sodium hydroxide and subjected to extraction with ethyl acetate. The organic layer was dried over magnesium sulfate and concentrated. The concentrate was purified by silica gel chromatography (chloroform) to afford 5-acetoxy-4,6-di-tert-butyl-2-hydroxybenzaldehyde (19.0 g).

m.p. 79.0° C. Mass 292(M$^+$), 250, 235, 217, 57

$^1$H NMR (60 MHz, CDCl$_3$) δ ppm 1.35(s,9H), 1.54(s, 9H), 2.35(s,3H), 6.92(s,1H), 10.67(s,1H), 12.32(s,1H)

IR (cm$^{-1}$) 2976, 1758

Reference Example 15

Synthesis of
4-Acetoxy-3,5-Di-tert-Butyl-2-(2-Ethyl-1-Butenyl)phenol

A solution of 3-bromopentane (1.3 g, 8.6 mmol) in tetrahydrofuran (10 ml) was added to magnesium (0.21 g, 8.6 mg atom) under a nitrogen atmosphere to prepare a Grignard reagent. A solution of 5-acetoxy-4,6-di-tert-butyl-2-hydroxydibenzaldehyde (1.0 g, 3.4 mmol) in tetrahydrofuran (5 ml) was added dropwise to the reagent. After stirring the mixture at room temperature for 30 min, a 5:2 mixed solution (7 ml) of water and conc. HCl was added to the reaction mixture, followed by stirring at room temperature for 30 min and subsequent extraction with ethyl acetate. The organic layer was dried over anhydrous magnesium sulfate and concentrated. The concentrate was purified by silica gel chromatography (10% ethyl acetate in n-hexane) to afford 4-acetoxy-3,5-di-tert-butyl-2-(2-ethyl-1-butenyl)phenol [0.85 g (yield, 72%)] as a yellow oil. Mass 346(M$^+$), 304, 289, 57

$^1$H NMR (60 MHz, CDCl$_3$) δ ppm 0.78–1.57(m,6H), 1.33(s,9H), 1.37(s,9H), 1.73–2.48(m,4H), 2.27(s,3H), 5.38(d,1H), 6.17(s,1H), 6.87(s,1H)

Example 12

Synthesis of
5-Acetoxy-4,6-Di-tert-Butyl-2,2-Diethyl-2,3-Dihydrobenzofuran

4-Acetoxy-3,5-di-tert-butyl-2-(2-ethyl-1-butenyl)phenol (0.85 g, 2.5 mmol) was dissolved in dichloromethane (10 ml) and BF$_3$ etherate (0.4 ml) was added dropwise to the solution under a nitrogen atmosphere. After stirring at room temperature for 3 h, water was added to the reaction mixture and extracted with ethyl acetate. The extracted layer was washed with a saturated aqueous solution of sodium hydrogen carbonate, dried over anhydrous magnesium sulfate and concentrated. The concentrate was purified by silica gel chromatography (10% ethyl acetate in n-hexane) to afford 5-acetoxy-4,6-di-tert-butyl-2,2-diethyl-2,3-dihydrobenzofuran [0.45 g (yield, 53%)] as a pale yellow oil. Mass 346(M$^+$), 304, 57

$^1$H NMR (60 MHz, CDCl$_3$) δ ppm 0.80–1.79(m,10H), 1.29(s,9H), 1.37(s,9H), 2.26(s,3H), 3.10(s,2H), 6.71(s,1H)

Example 13

Synthesis of
4,6-Di-tert-Butyl-2,2-Diethyl-5-Hydroxy-2,3-Dihydrobenzofuran (Compound d)

Lithium aluminum hydride (76 mg) was suspended in tetrahydrofuran (5 ml) under a nitrogen atmosphere. A solution of 5-acetoxy-4,6-di-tert-butyl-2,2-diethyl-2,3-dihydrobenzofuran (0.17 g, 0.5 mmol) in tetrahydrofuran (5 ml) was added dropwise to the suspension. After heating under reflux for 3 h, the reaction mixture was cooled to room temperature and water was added dropwise. After addition of 1N aqueous sodium hydroxide (5 ml), the mixture was subjected to extraction with diethyl ether. The organic layer was dried over anhydrous magnesium sulfate and concentrated. The concentrate was purified by silica gel chromatography (10% ethyl acetate in n-hexane) to afford 4,6-di-tert-butyl-2,2-diethyl-5-hydroxy-2,3-dihydrobenzofuran [130 mg (yield, 87%)] as a pale yellow oil. Mass 304(M$^+$), 289, 163, 57

$^1$H NMR (60 MHz, CDCl$_3$) δ ppm 0.92(t,3H), 1.20–1.87(m,8H), 1.43(s,9H), 1.51(s,9H), 3.17(s,2H), 4.62(s,1H), 6.62(s,1H)

IR (cm$^{-1}$) 3663, 2975

Similar procedures were taken to prepare the following compounds.

4,6-Di-tert-Butyl-2,2-Di-n-Propyl-5-Hydroxy-2,3-Dihydrobenzofuran (Compound e)

$^1$H NMR (60 MHz, CDCl$_3$) δ ppm 0.92(t,6H), 1.17–1.82(m,8H), 1.40(s,9H), 1.49(s,9H), 3.17(s,2H), 4.59(s,1H), 6.60(s,1H)

IR (cm$^{-1}$) 3662, 2971 Mass 332(M$^+$)

4,6-Di-tert-Butyl-2,2-Di-n-Butyl-5-Hydroxy-2,3-Dihydrobenzofuran (Compound f) Mass 360(M$^+$)

$^1$H NMR (60 MHz, CDCl$_3$) δ ppm 0.90(t,6H), 1.11–1.75(m,12H), 1.41(s,9H), 1.48(s,9H), 3.17(s,2H), 4.63(s,1H), 6.61(s,1H)

IR (cm$^{-1}$) 3663, 2964

4,6-Di-tert-Butyl-5-Hydroxy-2,3-Dihydrobenzofuran-2-Spiro-1'-Cyclopentane (Compound m)

m.p. 101.5° C. Mass 302(M$^+$)

$^1$H NMR (60 MHz, CDCl$_3$) δ ppm 1.40(s,9H), 1.49(s, 9H), 1.67–2.02(m,8H), 3.43(s,2H), 4.68(s,1H), 6.63(s,1H)

IR (cm$^{-1}$) 3644, 2979

4,6-Di-tert-Butyl-5-Hydroxy-2,3-Dihydrobenzofuran-2-Spiro-1'-cyclohexane (Compound n)

m.p. 124.5° C. Mass 316(M$^+$)

$^1$H NMR (60 MHz, CDCl$_3$) δ ppm 1.20–1.90(m,10H), 1.39(s,9H), 1.47(s,9H), 3.15(s,2H), 4.61(s,1H), 6.61(s,1H)

IR (cm$^{-1}$) 3650, 2934

4,6-Di-tert-Butyl-2,2-Diphenyl-5-Hydroxy-2,3-Dihydrobenzofuran (Compound j)

m.p. 115.3° C. Mass 400(M$^+$)

$^1$H NMR (60 MHz, CDCl$_3$) δ ppm 1.27(s,9H), 1.48(s, 9H), 4.72(s,1H), 4.91(d,1H,J=2.0 Hz), 5.26(d,1H, J=2,0 Hz), 6.88–7.41(m,11H)

IR (cm$^{-1}$) 3642, 2961

4,6-Di-tert-Butyl-5-Hydroxy-2,3-Dihydrobenzofuran-2-Spiro-1'-Cycloheptane (Compound o)

m.p. 91.6° C. Mass 344(M$^+$)

¹H NMR (60 MHz, CDCl₃) δ ppm 1.30–2.03(m,12H), 1.38(s,9H), 1.47(s,9H), 3.20(s,2H), 4.62(s,1H), 6.61(s,1H)

IR (cm⁻¹) 3646, 2927

4,6-Di-tert-Butyl-2,2-Dibenzyl-5-Hydroxy-2,3-Dihydrobenzofuran (Compound k)

m.p. 128.5° C. Mass 328(M⁺)

¹H NMR (60 MHz, CDCl₃) δ ppm 1.39(s,18H), 2.96(s,4H), 3.23(s,2H), 4.56(s,1H), 6.63(s,1H), 7.20(s,10H)

IR (cm⁻¹) 3661, 2970

4,6-Di-tert-Butyl-2,2-Di-i-Propyl-5-Hydroxy-2,3-Dihydrobenzofuran (Compound i) Mass 332(M⁺)

¹H NMR (60 MHz, CDCl₃) δ ppm 0.92(dd,12H,J=6.0 Hz), 1.39(s,9H), 1.50(s,9H), 2.01(m,2H), 3.10(s,2H), 5.52(s,1H), 6.52(s,1H)

IR (cm⁻¹) 3658, 2972

4,6-Di-tert-Butyl-5-Hydroxy-2,3-Dihydrobenzofuran-2-Spiro-1'-Cyclooctane (Compound p) Mass 344(M⁺)

¹H NMR (60 MHz, CDCl₃) δ ppm 1.40(s,9H), 1.47–1.94(m,14H), 1.50(s,9H), 3.18(s,2H), 4.67(s,1H), 6.63(s,1H)

IR (cm⁻¹) 3660, 2933

4,6-Di-tert-Butyl-5-Hydroxy-2,3-Dihydrobenzofuran-2-Spiro-4'-Tetrahydropyran m.p. 181.4° C. Mass 318(M⁺)

¹H NMR (60 MHz, CDCl₃) δ ppm 1.41(s,9H), 1.50(s,9H), 1.72–1.92(m,4H), 3.23(s,2H), 3.74–3.96(m,4H), 4.72(s,1H), 6.73(s,1H)

IR (cm⁻¹) 3365, 2972

4,6-Di-tert-Butyl-2,2-Di-n-Pentyl-5-Hydroxy-2,3-Dihydrobenzofuran (Compound x)

¹H NMR (270 MHz, CDCl₃) δ ppm 0.88(t,6H), 1.30(br,12H), 1.40(s,9H), 1.49(s,9H), 1.62(m,4H), 3.18(s,2H), 4.66(s,1H), 6.62(s,1H)

IR (cm⁻¹) 3652, 2956 Mass 388(M⁺)

4,6-Di-tert-Butyl-2,2-Di-n-Octyl-5-Hydroxy-2,3-Dihydrobenzofuran (Compound y)

¹H NMR (270 MHz, CDCl₃) δ ppm 0.88(m,6H), 1.26(bs,24H), 1.40(s,9H), 1.49(s,9H), 1.59–1.65(m,4H), 3.18(s,2H), 4.66(s,1H), 6.62(s,1H) Mass 472(M⁺)

4,6-Di-tert-Butyl-2,2-Di-n-Heptyl-5-Hydroxy-2,3-Dihydrobenzofuran

¹H NMR (270 MHz, CDCl₃) δ ppm 0.87(t,6H), 1.27(br,20H), 1.40(s,9H), 1.49(s,9H), 1.62(m,4H), 3.18(s,2H), 4.66(s,1H), 6.62(s,1H)

IR (cm⁻¹) 3656, 2928 Mass 444(M⁺)

4,6-Di-tert-Butyl-2,2-Di-n-Hexyl-5-Hydroxy-2,3-Dihydrobenzofuran

¹H NMR (270 MHz, CDCl₃) δ ppm 0.87(t,6H), 1.28(br,16H), 1.40(s,9H), 1.49(s,9H), 1.63(m,4H), 3.19(s,2H), 4.65(s,1H), 6.62(s,1H)

IR (cm⁻¹) 3650, 2920 Mass 416(M⁺)

Reference Example 16

Synthesis of 2,6-Di-tert-Butyl-3-Methyl-4-Tetrahydropyranyloxyphenol 2,6-di-tert-butyl-3-methyl-1,4-benzoquinone (49 g) was dissolved in methylene chloride (300 ml) and sodium borohydride (15 g) was added to the solution under a nitrogen atmosphere. After adding methanol (30 ml) dropwise, the mixture was stirred for 3 h, poured into 5% HCl under ice cooling, and subjected to extraction with methylene chloride. The extract was washed with water, dried over anhydrous sodium sulfate and the solvent was distilled off. The residue was dissolved in methylene chloride (200 ml) and, after adding 3,4-2H-dihydropyran (26 ml) and a catalytic amount of paratoluenesulfonic acid, the mixture was stirred overnight at room temperature. The reaction mixture was washed with water, dried over anhydrous sodium sulfate and the solvent was distilled off. The residue was purified by silica gel chromatography (10% ethyl acetate in n-hexane) to afford 2,6-di-tert-butyl-3-methyl-4-tetrahydropyranyloxyphenol [54.4 g (yield, 81%)] as a colorless oil. Mass 320(M⁺)

¹H NMR (60 MHz, CDCl₃) δ ppm 0.8–1.9(br,6H), 1.39(s,9H), 1.56(s,9H), 3.6–4.0(m,2H), 2.37(s,3H), 4.95(s,1H), 5.15(br,1H), 6.98(s,1H)

Reference Example 17

Synthesis of 1-Acetoxy-2,6-Di-tert-Butyl-3-Methyl-4-Tetrahydropyranyloxybenzene 2,6-Di-tert-butyl-3-methyl-4-tetrahydropyranyloxyphenol (4.4 g) was dissolved in anhydrous tetrahydrofuran (50 ml) and a n-hexane solution (1.1 eq.) of n-butyllithium was added dropwise at 0° C. under a nitrogen atmosphere. After stirring the mixture for 30 min, acetyl chloride (1.08 ml, 1.1 eq.) was added and the mixture was allowed to warm to room temperature. After stirring for 3 h, the reaction mixture was poured into a saturated aqueous solution of ammonium chloride and the mixture was subjected to extraction with diethyl ether. The extract was washed with water and saturated brine, then dried over anhydrous sodium sulfate and the solvent was distilled off. The residue was purified by silica gel chromatography (10% ethyl acetate in n-hexane) to afford 1-acetoxy-2,6-di-tert-butyl-3-methyl-4-tetrahydropyranyloxybenzene [4.09 g (yield, 82.2%)] as a colorless crystal. Mass 362(M⁺)

¹H NMR (60 MHz, CDCl₃) δ ppm 0.8–1.8(br,6H), 1.30(s,9H), 1.42(s,9H), 2.26(s,3H), 2.35(s,3H), 3.4–4.1(m,2H), 5.28(m,1H), 7.07(s,1H)

Reference Example 18

Synthesis of 4-Acetoxy-3,5-Di-tert-Butyl-2-Methylphenol

1-Acetoxy-2,6-di-tert-butyl-3-methyl-4-tetrahydropyranyloxybenzene (4.09 g) was dissolved in tetrahydrofuran (20 ml). After adding 10% HCl (3 ml), the mixture was stirred at room temperature for 3 h. The reaction mixture was poured into water and subjected to extraction with diethyl ether. The extract was washed with 5% aqueous sodium hydrogen carbonate and saturated brine, then dried over anhydrous sodium sulfate and the solvent was distilled off. The residue was recrystallized from n-hexane to afford 4-acetoxy-3,5-di-tert-butyl-2-methylphenol (3.1 g) as a colorless needle.

¹H NMR (60 MHz, CDCl₃) δ ppm 1.31(s,9H), 1.44(s, 9H), 2.30(s,3H), 2.35(s,3H), 4,73(s,1H), 6.72(s,1H)

Example 14

Synthesis of
1-Acetoxy-2,6-Di-tert-butyl-3-Methyl-4-propyloxybenzene

Sodium hydride (100 mg) was suspended in N,N-dimethylformamide (5 ml) and a solution of 4-acetoxy-3,5-di-tert-butyl-2-methylphenol (0.5 g) in N,N-dimethylformamide (5 ml) was added dropwise to the suspension at 0° C. After stirring for 20 min, propyl bromide (0.2 ml) was added and the mixture was stirred for an additional 2 h. The reaction mixture was then poured into a saturated aqueous solution of ammonium chloride and extracted with diethyl ether. The extract was washed with water and saturated brine, then dried over anhydrous sodium sulfate. The solvent was distilled off to afford 1-acetoxy-2,6-di-tert-butyl-3-methyl-4-propyloxybenzene which was substantially pure on TLC. It was used in the subsequent reaction without further purification.

¹H NMR (60 MHz, CDCl₃) δ ppm 1.33(s,9H), 1.45(s, 9H), 1.84(m,2H), 2.27(s,3H), 2.34(s,3H), 3.87(m,2H), 6.74(s,1H)

Example 15

Synthesis of
2,6-Di-tert-Butyl-3-Methyl-4-Propyloxyphenol
(Compound u)

Lithium aluminum hydride (100 mg) was suspended in tetrahydrofuran (5 ml) under a nitrogen atmosphere. A solution of the 1-acetoxy-2,6-di-tert-butyl-3-methyl-4-propyloxybenzen in tetrahydrofuran (5 ml) was added to the suspension and the mixture was refluxed for 3 h. A saturated aqueous solution of ammonium chloride was added to the reaction mixture under ice cooling and the precipitate was filtered off together with the anhydrous sodium sulfate. The filtrate was concentrated and purified by silica gel chromatography (10% ethyl acetate in n-hexane) to afford 2,6-di-tert-butyl-3-methyl-4-propyloxyphenol (150 mg) as a colorless oil. Mass 278(M⁺)

¹H NMR (60 MHz, CDCl₃) δ ppm 1.06(t,3H,J=6 Hz), 1.45(s,9H), 1.61(s,9H), 1.80(m,2H), 2.38(s,3H), 3.85(t,2H, J=6 Hz), 4.90(s,1H), 6.75(s,1H)

Example 16

Synthesis of
1-Acetoxy-4-Allyloxy-2,6-Di-tert-Butyl-3-Methylbenzene and
1,3-Bis(4-Acetoxy-3,5-Di-tert-Butyl-2-Mehtylphenoxy)propane Sodium hydride (110 mg) was suspended in N,N-dimethylformamide (5 ml) and a solution of 4-acetoxy-3,5-di-tert-butyl-2-methylphenol (0.6 g) in N,N-dimethylformamide (5 ml) was added dropwise to the suspension at 0° C. After stirring for 30 min, 1,3-dibromopropane (0.36 ml) was added in one portion and the mixture was stirred for an additional 2 h. The reaction mixture was poured into a saturated aqueous solution of ammonium chloride and subjected to extraction with diethyl ether. The extract was washed with water and saturated brine, then dried over anhydrous sodium sulfate and the solvent was distilled off.

The residue was dissolved in N,N-dimethylformamide (5 ml) and added to a solution prepared in the same manner as described above (4-acetoxy-3,5-di-tert-butyl-2-methylphenol, 0.4 g; sodium hydride, 86 mg; N,N-dimethylformamide, 5 ml). The mixture was allowed to warm from 0° C. to room temperature and stirred for 2 h. Subsequently, it was poured into a saturated aqueous solution of ammonium chloride and treated as described above. The residue was purified by silica gel chromatography (10% ethyl acetate in n-hexane). The first fraction gave 1-acetoxy-4-allyloxy-2,6-di-tert-butyl-3-methylbenzene (370 mg). The next fraction gave 1,3-bis(4-acetoxy-3,5-di-tert-butyl-2-methylphenoxy)propane (200 mg).

1-Acetoxy-4-Allyloxy-2,6-Di-tert-Butyl-3-Methylbenzene

¹H NMR (60 MHz, CDCl₃) δ ppm 1.30(s,9H), 14.2(s, 9H), 2.25(s,3H), 2.35(s,3H), 4.44(m,2H), 5.0–5.5(m,2H), 5.83–6.43(m,1H), 6.72(s,1H)

1,3-Bis(4-Acetoxy-3,5-Di-tert-Butyl-2-Methylphenoxy)propane

¹H NMR (60 MHz, CDCl₃) δ ppm 1.32(s,18H), 1.37(s, 18H), 1,85(m,2H), 2.25(s,6H), 2.33(s,6H), 4.12(m,4H), 6.76(s,2H)

Example 17

Synthesis of
4-Allyloxy-2,6-Di-tert-Butyl-3-Methylphenol
(Compound v)

1-Acetoxy-4-allyloxy-2,6-di-tert-butyl-3-methylbenzene was treated as in Example 15 to afford 4-allyloxy-2,6-di-tert-butyl-3-methylphenol quantitatively as a pale yellow oil. Mass 276(M⁺)

¹H NMR (60 MHz, CDCl₃) δ ppm 1.39(s,9H), 1.58(s, 9H), 2.33(s,3H), 4.84(s,1H), 4.35(m,2H), 5.0–5.5(m,2H), 5.7–6.3(m,1H), 6.64(s,1H)

Example 18

Synthesis of 1,3-Bis(3,5-Di-tert-Butyl-4-Hydroxy-2-Methylphenoxy)propane (Compound w)

1,3-Bis(4-acetoxy-3,5-di-tert-butyl-2-methylphenoxy)propane was treated as in Example 15 to afford 1,3-bis(3,5-di-tert-butyl-4-hydroxy-2-methylphenoxy)propane as a colorless crystal in 76% yield. Mass 512(M⁺)

¹H NMR (60 MHz, CDCl₃) δ ppm 1.42(s,18H), 1.60(s, 18H), 2.15–2.4(m,2H), 2.35(s,6H), 4.06(t,4H,J=6 Hz), 4.90(s,2H), 6.72(s,2H)

m.p. 120.4° C.

Example 19

Synthesis of
3-Acetoxy-2,4-Di-tert-Butyl-6-Hydroxy-5-Methylbenzaldehyde

4-Acetoxy-3,5-di-tert-butyl-2-methylphenol was treated as in Reference Example 13 or 14 or in Example 11 to afford 3-acetoxy-2,4-di-tert-butyl-6-hydroxy-5-methylbenzaldehyde as a pale yellow crystal in 7% overall yield. Mass 292(M⁺)

¹H NMR (60 MHz, CDCl₃) δ ppm 1.44(s,9H), 1.50(s, 9H), 2.27(s,3H), 2.35(s,3H), 10.54(s,1H), 12.66(s,1H)

Reference Example 19

Synthesis of 4-tert-Butyl-5-Hydroxy-2-Methylbenzofuran

5-Benzyloxy-4-tert-butyl-2-formylbenzofuran (700 mg, 2.3 mmol) was dissolved in acetic acid (30 ml) and, after addition of 10% Pd on carbon (700 mg), the solution was stirred under a hydrogen atmosphere (5 atm.) for 8 h. After filtering off the Pd on carbon, the filtrate was washed with a saturated aqueous solution of sodium hydrogen carbonate, dried over anhydrous magnesium sulfate and concentrated. The concentrate was subjected to silica gel chromatography and eluted with a solvent system consisting of a 4:1 mixture of hexane and ethyl acetate to afford 4-tert-butyl-5-hydroxy-2-methylbenzofuran [320 mg (yield, 68%)] as a pale yellow, fine-grained crystal.

m.p. 49.9° C. Mass 204(M$^+$), 189

$^1$H NMR (60 MHz, CDCl$_3$) δ ppm 1.48(s,9H), 2.29(s, 3H), 4.87(s,1H), 6.43 (d,1H,J=8.8 Hz), 6.60(s,1H), 6.98(d, 1H,J=8.8 Hz)

Example 20

Synthesis of 4,6-Di-tert-Butyl-5-Hydroxy-2-Methylbenzofuran (Compound s)

Methanesulfonic acid (1.2 ml) was added dropwise to a chloroform solution of 4-tert-butyl-5-hydroxy-2-methylbenzofuran (250 mg, 1.2 mmol) and tert-butyl alcohol (500 mg, 6.0 mmol) under cooling with ice. After stirring at 0° C. for 15 min, the mixture was poured into ice water. The mixture was then neutralized with 1N aqueous sodium hydroxide and subjected to extraction with ethyl acetate. The extracted layer was washed with a saturated aqueous solution of sodium hydrogen carbonate, dried over anhydrous magnesium sulfate and concentrated. The concentrate was purified by silica gel chromatography (n-hexane) to afford 4,6-di-tert-butyl-5-hydroxy-2-methylbenzofuran (35 mg) as a pale yellow oil. Mass 260(M$^+$), 245, 57

$^1$H NMR (60 MHz, CDCl$_3$) δ ppm 1.46(s,9H), 1.61(s, 9H), 2.37(s,3H), 5.07(s,1H), 6.63(s,1H), 7.27(s,1H)

IR (cm$^{-1}$) 3651, 2964

Reference Example 20

Synthesis of 4-Acetoxy-3,5-Di-tert-Butyl-2-(1'-Hydroxy-2',6',10',14'-Tetramethylpentadecyl)phenol A solution of 2-bromo-6,10,14-trimethylpentadecane (3.4 g, 10.2 mmol) in tetrahydrofuran (15 ml) was added to magnesium (0.25 g, 10.2 mg atom) under a nitrogen atmosphere to prepare a Grignard reagent. A solution of 5-acetoxy-4,6-di-tert-butyl-2-hydroxybenzaldehyde (1.0 g, 3.4 mmol) in tetrahydrofuran (5 ml) was added dropwise to the reagent. After stirring the reaction mixture at room temperature for 30 min, a saturated aqueous solution of ammonia chloride was added and the mixture was subjected to extraction with ethyl acetate. The organic layer was dried over anhydrous magnesium sulfate and concentrated. The concentrate was purified by silica gel chromatography (10% ethyl acetate in n-hexane) to afford 4-acetoxy-3,5-di-tert-butyl-2-(1'-hydroxy-2',6',10',14'-tetramethylpentadecyl)phenol [0.11 g (yield, 6%)] as a colorless oil. Mass 486(M$^+$), 57

$^1$H NMR (60 MHz, CDCl$_3$) δ ppm 0.85(d,15H), 1.02–1.95(m,22H), 1.27(s,9H), 1.37(s,9H), 2.23(s,3H), 2.95(d,1H,J=3.4 Hz), 5.08(dd,1H,J=3.4 Hz,J=9.6 Hz), 6.73(s,1H), 7.88(s,1H)

Example 21

Synthesis of 4,6-Di-tert-Butyl-5-Hydroxy-2-Methyl-2-(4',8',12'-Trimethyltridecyl)-2,3-Dihydrobenzofuran 4-Acetoxy-3,5-di-tert-butyl-2-(1'-hydroxy-2',6',10',14'-tetramethylpentadecyl)phenol (0.11 g, 0.2 mmol) was dissolved in dichloromethane (5 ml) and BF$_3$ etherate (0.2 ml) was added dropwise to the solution under a nitrogen atmosphere. After stirring the mixture at room temperature for 24 h, water was added and the mixture was subjected to extraction with ethyl acetate. The extracted layer was washed with a saturated aqueous solution of sodium hydrogen carbonate, dried over anhydrous magnesium sulfate and concentrated. The concentrate was dissolved in tetrahydrofuran (3 ml) and added dropwise to a suspension of lithium aluminum hydride (10 mg) in tetrahydrofuran (2 ml) under a nitrogen atmosphere. After refluxing for 2 h, the mixture was cooled to room temperature and water was added dropwise. After adding 1N aqueous sodium hydroxide (5 ml), the mixture was subjected to extraction with diethyl ether. The organic layer was dried over anhydrous magnesium sulfate and concentrated. The concentrate was purified by silica gel chromatography (n-hexane) to afford 4,6-di-tert-butyl-5-hydroxy-2-methyl-2-(4',8',12'-trimethyldecyl)-2,3-dihydrobenzofuran [54 mg (yield, 56%)] as a colorless oil. Mass 486(M$^+$), 471, 149, 57

$^1$H NMR (270 MHz, CDCl$_3$) δ ppm 0.83–0.88(m,12H), 1.08–1.64(m,18H), 1.36(s,3H), 1.41(s,9H), 1.49(s,9H), 3.14(d,1H,J=15.7 Hz), 3.27(d,1H,J=15.7 Hz), 4.68(s,1H), 6.63(s,1H)

IR (cm$^{-1}$) 3656, 2956

Reference Example 21

Synthesis of 4-Acetoxy-3,5-Di-tert-Butyl-2-(2,2-Diisoamyl-1-Hydroxyethyl)phenol Lithium (2.8 g) was added to a solution of 5-acetoxy-4,6-di-tert-butyl-2-hydroxybenzaldehyde (24.3 g) and 5-bromo-2,8-dimethylnonane (47.0 g) in tetrahydrofuran (200 ml) under ice cooling under a nitrogen atmosphere and the mixture was stirred overnight. The reaction mixture was poured into ice water, neutralized with a saturated aqueous solution of ammonium chloride and subjected to extraction with diethyl ether. The extract was washed with saturated brine, dried over anhydrous magnesium sulfate and the solvent was distilled off. The residue was purified by silica gel chromatography (10% ethyl acetate in n-hexane) to afford 4-acetoxy-3,5-di-tert-butyl-2-(2,2-diisoamyl-1-hydroxyethyl)phenol [17.0 g (yield, 46%)] as a colorless oil.

$^1$H NMR (60 MHz, CDCl$_3$) δ ppm 0.80–1.81(m,11H), 0.87(d,12H), 1.25(s,9H), 1.37(s,9H), 2.24(s,3H), 3.51(br, 1H), 5.19(d,1H), 6.72(s,1H), 7.92(s,1H) Mass 448(M$^+$)

Example 22

Synthesis of 5-Acetoxy-2,2-Diisoamyl-4,6-Di-tert-Butyl-2,3-Dihydrobenzofuran BF$_3$ etherate (4.7 ml) was added dropwise to a solution of 4-acetoxy-3,5-di-tert-butyl-2-(2,2-diisoamyl-1-hydroxyethyl)-phenol (17.0 g) in dichloromethane (200 ml) under cooling with ice under a nitrogen atmosphere. After stirring the mixture overnight at room temperature, a saturated aqueous solution of sodium hydrogen carbonate was added. After separating the organic layer, the aqueous layer was subjected to extraction with dichloromethane. The extract was combined with the organic layer, washed with saturated brine, dried over anhydrous magnesium sulfate and the solvent was distilled off to afford 5-acetoxy-2,2-diisoamyl-4,6-di-tert-butyl-2,3-dihydrobenzofuran [15.5 g (yield, 95%)] as a colorless oil.

$^1$H NMR (60 MHz, CDCl$_3$) δ ppm 0.87(d,12H), 1.04–1.93(m,10H), 1.28(s,9H), 1.35(s,9H), 2.25(s,3H), 3.14(s,2H), 6.67(s,1H)

IR (cm$^{-1}$) 2956, 1764 Mass 430(M$^+$)

Example 23

Synthesis of 2,2-Diisoamyl-4,6-Di-tert-Butyl-5-Hydroxy-2,3-Dihydrobenzofuran (Compound z)

Lithium aluminum hydride (1.90 g) was suspended in tetrahydrofuran (200 ml) under a nitrogen atmosphere. A solution of 5-acetoxy-2,2-diisoamyl-4,6-di-tert-butyl-2,3-dihydrobenzofuran (17.4 g) in tetrahydrofuran (60 ml) was added dropwise to the suspension under cooling with ice. After heating under reflux overnight, the mixture was cooled to room temperature and water and a saturated aqueous solution of ammonium chloride were added in that order. The resulting insolubles were filtered off on Celite. The filtrate was subjected to extraction with diethyl ether, washed with saturated brine, dried over anhydrous magnesium sulfate and the solvent was distilled off. The residue was purified by silica gel chromatography (n-hexane) to afford 2,2-diisoamyl-4,6-di-tert-butyl-5-hydroxy-2,3-dihydrobenzofuran [9.0 g (yield, 57%)] as a colorless oil.

$^1$H NMR (270 MHz, CDCl$_3$) δ ppm 0.89(d,12H), 1.19–1.69(m,10H), 1.41(s,9H), 1.49(s,9H), 3.17(s,2H), 4.66(s,1H), 6.62(s,1H)

IR (cm$^{-1}$) 3652, 2956 Mass 388(M$^+$)

Example 24

Synthesis of 4,6-Di-tert-Butyl-5-Hydroxy-2,3-Dihydrobenzofuran

1) Synthesis of 4-Acetoxy-3,5-Di-tert-Butyl-2-(2-Propenyl)anisole

4-Acetoxy-3,5-di-tert-butyl-2-(2-propenyl)phenol (30 g) and potassium carbonate (13.8 g) were dissolved in acetone (300 ml) and, after addition of methyl iodide (28 g), the solution was stirred for 24 h. After cooling, the reaction mixture was concentrated under reduced pressure and water was added. The mixture was then subjected to extraction with ethyl acetate and the organic layer was washed with water and saturated brine, dried over anhydrous magnesium sulfate and concentrated. The concentrate was purified by silica gel chromatography (10% ethyl acetate in n-hexane) to afford 4-acetoxy-3,5-di-tert-butyl-2-(2-propenyl)anisole (31 g) quantitatively.

$^1$H NMR (270 MHz, CDCl$_3$) δ ppm 1.34(s,9H), 1.43(s,9H), 2.30(s,3H), 3.63–3.68(m,2H), 3.78(s,3H), 4.88–5.02(m,2H), 5.89–6.02(m,1H), 6.83(s,1H) Mass 318(M$^+$)

2) Synthesis of 4-Acetoxy-3,5-Di-tert-Butyl-2-Formylmethylanisole

4-Acetoxy-3,5-di-tert-butyl-2-(2-propenyl)anisole (19 g) was dissolved in a 1:1 mixture (200 ml) of tetrahydrofuran and water. After adding osmium tetroxide (0.12 g) and sodium periodate (26.9 g), the mixture was stirred at room temperature for 48 h. After the end of the reaction, a saturated aqueous solution of sodium thiosulfate was added and the mixture was subjected to extraction with ethyl acetate and the organic layer was washed with water and saturated brine, dried over anhydrous magnesium sulfate and concentrated. The concentrate was purified by silica gel chromatography (25% ethyl acetate in n-hexane) to afford 4-acetoxy-3,5-di-tert-butyl-2-formylmethylanisole [16 g (yield, 83%)].

$^1$H NMR (60 MHz, CDCl$_3$) δ ppm 1.36(s,9H), 1.40(s,9H), 2.30(s,3H), 3.77(s,3H), 3.87(bs,2H), 6.89(s,1H), 9.63(bs,1H) Mass 320(M$^+$)

3) Synthesis of 5-Acetoxy-4,6-Di-tert-Butylbenzofuran

4-Acetoxy-3,5-di-tert-butyl-2-formylmethylanisole (16 g) was dissolved in dichloromethane (100 ml) and trimethylsilyl iodide (7.1 ml) was added dropwise to the solution under cooling with ice. After stirring the mixture at room temperature for 1 h, a saturated aqueous solution of sodium thiosulfate was added and the mixture was subjected to extraction with chloroform. The organic layer was washed with water and saturated brine, dried over anhydrous magnesium sulfate and concentrated. The concentrate was purified by silica gel chromatography (10% ethyl acetate in n-hexane) to afford 5-acetoxy-4,6-di-tert-butylbenzofuran quantitatively (14.3 g) as a white solid.

$^1$H NMR (270 MHz, CDCl$_3$) δ ppm 1.39(s,9H), 1.51(s,9H), 2.35(s,3H), 6.98(d,1H,J=2.3 Hz), 7.46(s,1H), 7.55 (d,1H,J=2.3 Hz) Mass 288(M$^+$)

m.p. 87.7° C.

4) Synthesis of 4,6-Di-tert-Butyl-5-Hydroxybenzofuran (Compound r)

Lithium aluminum hydride (1.31 g) was suspended in tetrahydrofuran (150 ml) under a nitrogen atmosphere. A solution of 5-acetoxy-4,6-di-tert-butylbenzofuran (10 g) in tetrahydrofuran (100 ml) was added dropwise to the suspension under cooling with ice. After heating under reflux for 3 h, the mixture was cooled to room temperature and, after addition of water and 10% aqueous HCl (100 ml), the mixture was subjected to extraction with ethyl acetate. The organic layer was dried over anhydrous magnesium sulfate and concentrated. The concentrate was purified by silica gel chromatography (10% ethyl acetate in n-hexane) to afford 4,6-di-tert-butyl-5-hydroxybenzofuran [8.3 g (yield, 98%)].

5) Synthesis of 4,6-Di-tert-Butyl-5-Hydroxy-2,3-Dihydrobenzofuran (Compound a)

4,6-Di-tert-butyl-5-hydroxybenzofuran (6.0 g) was dissolved in acetic acid (50 ml). After addition of 10% Pd on carbon (5.0 g), the solution was stirred under a hydrogen atmosphere (4 atm.) for 15 min. After filtering off the Pd on carbon, the filtrate was concentrated under vacuum. The concentrate was purified by silica gel chromatography (10% ethyl acetate in n-hexane) to afford 4,6-di-tert-butyl-5-hydroxy-2,3-dihydrobenzofuran [4.4 g (yield, 73%)] as a colorless, fine-grained crystal.

Example 25

Synthesis of 4,6-Di-tert-Butyl-5-Hydroxy-2-Octyl-2,3-Dihydrobenzofuran

1) Synthesis of 5-Acetoxy-4,6-Di-tert-Butyl-2-Formylbenzofuran

Phosphorus oxychloride (1.1 g) was added dropwise to N,N-dimethylformamide (0.4 g) under cooling with ice and, subsequently, a solution of 5-acetoxy-4,6-di-tert-butylbenzofuran (1.0 g) in N,N-dimethylformamide (2 ml) was added dropwise. The mixture was stirred first at room temperature for 20 min, then under heating at 80° C. for 75 min. After cooling, the reaction mixture was poured into water and subjected to extraction ethyl acetate. The organic layer was washed with water and saturated brine, dried over anhydrous magnesium sulfate and concentrated. The concentrate was purified by silica gel chromatography (10% ethyl acetate in n-hexane) to afford 5-acetoxy-4,6-di-tert-butyl-2-formylbenzofuran [0.95 g (yield, 86%)] as a colorless, fine-grained crystal.

$^1$H NMR (60 MHz, CDCl$_3$) δ ppm 1.40(s,9H), 1.54(s, 9H), 2.37(s,3H), 7.57(s,1H), 7.83(s,1H), 9.88(s,1H) Mass 316(M$^+$)

m.p. 159.9° C.

2) Synthesis of 5-Acetoxy-4,6-Di-tert-Butyl-2-(1-Octenyl)benzofuran

A pentane solution (6.0 ml) of 1.6M n-butyllithium was added dropwise to a solution of n-heptyltriphenylphosphonium bromide (4.2 g) in tetrahydrofuran (30 ml) under a nitrogen atmosphere. After stirring the mixture at room temperature for 90 min, a solution of 5-acetoxy-4,6-di-tert-butyl-2-formylbenzofuran (2.54 g) in tetrahydrofuran (20 ml) was added dropwise. Subsequently, the mixture was heated under reflux for 1 h and, after cooling, a saturated aqueous solution of ammonium chloride was added and the mixture was subjected to extraction with ethyl acetate. The organic layer was washed with water and saturated brine, dried over anhydrous magnesium sulfate and concentrated. The concentrate was purified by silica gel chromatography (10% ethyl acetate in n-hexane) to afford 5-acetoxy-4,6-di-tert-butyl-2-(1-octenyl)benzofuran [3.1 g (yield, 97%)] as a colorless oil.

$^1$H NMR (60 MHz, CDCl$_3$) δ ppm 0.88(t,3H), 1.15–1.54(m,8H), 1.37(s,9H), 1.48(s,9H), 2.31(s,3H), 2.51(m,2H), 6.10(m,1H), 6.27(m,1H), 6.67(s,1H), 7.33(s, 1H) Mass 398(M$^+$)

3) Synthesis of 5-Acetoxy-4,6-Di-tert-Butyl-2-Octylbenzofuran

5-Acetoxy-4,6-di-tert-butyl-2-(1-octenyl)benzofuran (3.1 g) was dissolved in ethyl acetate containing 10% acetic acid (50 ml) and, after addition of 10% Pd on carbon (0.3 g), the solution was stirred under a hydrogen atmosphere for 3 h. After filtering off the Pd on carbon, the filtrate was concentrated under vacuum. The concentrate was purified by silica gel chromatography (10% ethyl acetate in n-hexane) to afford 5-acetoxy-4,6-di-tert-butyl-2-octylbenzofuran [2.95 g (yield, 96%)] as a colorless oil.

$^1$H NMR (60 MHz, CDCl$_3$) δ ppm 0.88(t,3H), 1.17–1.57(m,12H), 1.35(s,9H), 1.47(s,9H), 2.29(s,3H), 2.70(t,2H,J=7.0 Hz), 6.56(s,1H), 7.35(s,1H) Mass 400(M$^+$)

4) Synthesis of 4,6-Di-tert-Butyl-5-Hydroxy-2-Octylbenzofuran

Lithium aluminum hydride (0.26 g) was suspended in tetrahydrofuran (50 ml) under a nitrogen atmosphere and a solution of 5-acetoxy-4,6-di-tert-butyl-2-octylbenzofuran (2.7 g) in tetrahydrofuran (20 ml) was added to the suspension under cooling with ice. After heating under reflux for 3 h, the mixture was cooled to room temperature and water was added dropwise. After adding 10% aqueous HCl (50 ml), the mixture was subjected to extraction with ethyl acetate. The organic layer was dried over anhydrous magnesium sulfate and concentrated. The concentrate was purified by silica gel chromatography (10% ethyl acetate in n-hexane) to afford 4,6-di-tert-butyl-5-hydroxybenzofuran [2.2 g (yield, 92%)] as a colorless oil.

$^1$H NMR (60 MHz, CDCl$_3$) δ ppm 0.88(t,3H), 1.20–1.53(m,12H), 1.45(s,9H), 1.61(s,9H), 2.67(t,2H,J=7.0 Hz), 5.03(s,1H), 6.58(s,1H), 7.21(s,1H) Mass 358(M$^+$)

IR (cm$^{-1}$) 3384, 2928

5) Synthesis of 4,6-Di-tert-Butyl-5-Hydroxy-2-Octyl-2,3-Dihydrobenzofuran (Compound g)

Triethylsilane (17.4 ml) was added to 4,6-di-tert-butyl-5-hydroxy-2-octylbenzofuran (2.2 g) and trifluoroacetic acid (8.7 ml) was added dropwise to the mixture under cooling with ice. After stirring at 0° C. for 1 h, the mixture was poured into ice water and subjected to extraction with ethyl acetate. The organic layer was washed with a saturated aqueous solution of sodium hydrogen carbonate, dried over anhydrous magnesium sulfate and concentrated. The concentrate was purified by silica gel chromatography (n-hexane) to afford 4,6-di-tert-butyl-5-hydroxy-2-octyl-2,3-dihydrobenzofuran [0.6 g (yield, 27%)].

Reference Example 22

Synthesis of 4-Acetoxy-2-Acetonyl-3,5-Di-tert-Butylanisole

Palladium chloride (2.96 g) and copper chloride (16.5 g) were added to a solvent system (88 ml) consisting of a 7:1 mixture of N,N-dimethylformamide and water under an oxygen atmosphere and the resulting mixture was stirred at room temperature for 1 h. Subsequently, a solution of 4-acetoxy-3,5-di-tert-butyl-2-(2-propenyl)phenol (53.2 g) in a solvent system (48 ml) consisting of a 7:1 mixture of N,N-dimethylformamide and water was added and the resulting mixture was stirred at room temperature for 48 h. After the end of the reaction, water was added to the reaction mixture, which was then subjected to extraction with ethyl acetate. The organic layer was washed with water and saturated brine, dried over anhydrous magnesium sulfate and concentrated. The concentrate was purified by silica gel chromatography (25% ethyl acetate in n-hexane) to afford 4-acetoxy-2-acetonyl-3,5-di-tert-butylanisole [33 g (yield, 59%)] as a colorless, fine-grained crystal.

$^1$H NMR (270 MHz, CDCl$_3$) δ ppm 1.34(s,9H), 1.40(s, 9H), 2.20(s,3H), 2.31(s,3H), 3.74(s,3H), 3.90(d,1H,J=7.8 Hz), 4.02(d,1H,J=17.8 Hz), 6.83(s,1H) Mass 334(M$^+$)

m.p. 133.2° C.

Reference Example 23

Synthesis of 4-Acetoxy-2-[4-(1,3-Dioxa-2-Cyclopentyl)-2-Hydroxy-2-Methylbutyl]-3,5-Di-tert-Butylanisole A solution of 2-(2-bromoethyl)-1,3-dioxane (50 g) in tetrahydrofuran (200 ml) was added to magnesium (6.6 g) under a nitrogen atmosphere to prepare a Grignard reagent. A solution of 4-acetoxy-2-acetonyl-3,5-di-tert-butylanisole in tetrahydrofuran (200 ml) was added dropwise to the reagent. After stirring the mixture at room temperature for 3 h, a saturated aqueous solution of ammonium chloride was added and the resulting mixture was subjected to extraction with ethyl acetate. The organic layer was washed with water and saturated brine, dried over anhydrous magnesium sulfate and concentrated. The concentrate was purified by silica gel chromatography (33% ethyl acetate in n-hexane) to afford 4-acetoxy-2-[4-(1,3-dioxa-2-cyclopentyl)-2-hydroxy-2-methylbutyl]-3,5-di-tert-butylanisole [27.9 g (yield, 69%)] as a colorless oil.

$^1$H NMR (270 MHz, CDCl$_3$) δ ppm 1.33(s,9H), 1.36(s, 9H), 1.38(s,3H), 1.52–1.89(m,4H), 2.28(s,3H), 3.26(s,2H), 3.73–3.88(m,2H), 3.82(s,3H), 4.06–4.15(m,3H), 4.56(t,1H), 6.82(s,1H) Mass 436(M$^+$)

Example 26

Synthesis of
5-Acetoxy-2-[2-(1,3-Dioxa-2-Cyclopentyl)ethyl]-4,6-Di-tert-Butyl-2-Methyl-2,3-Dihydrobenzofuran 4-Acetoxy-2-[4-(1,3-dioxa-2-cyclopentyl)-2-hydroxy-2-methylbutyl]-3,5-di-tert-butylanisole (27.9 g) was dissolved in dichloromethane (200 ml) and trimethylsilyl iodide (12.8 ml) was added dropwise to the solution under cooling with ice. After stirring the mixture at room temperature for 5 min, a saturated aqueous solution of sodium thiosulfate was added and the mixture was subjected to extraction with chloroform. The organic layer was washed with water and saturated brine, dried over anhydrous magnesium sulfate and concentrated. The concentrate was purified by silica gel chromatography (25% ethyl acetate in n-hexane) to afford 5-acetoxy-2-[2-(1,3-dioxa-2-cyclopentyl)ethyl]-4,6-di-tert-butyl-2-methyl-2,3-dihydrobenzofuran [17.3 g (yield, 67%)] as a colorless oil.

$^1$H NMR (270 MHz, CDCl$_3$) δ ppm 1.29(s,9H), 1.36(s, 9H), 1.37(s,3H), 1.69–1.83(m,4H), 2.29(s,3H), 3.06–3.33(m,2H), 3.75(t,2H), 4.07–4.13(m,2H), 4.51–4.56(m,1H), 6.70(s,1H) Mass 404(M$^+$)

Example 27

Synthesis of
5-Acetoxy-4,6-Di-tert-Butyl-2-(2-Formylethyl)-2-Methyl-2,3-Dihydrobenzofuran 5-Acetoxy-2-[2-(1,3-dioxa-2-cyclopentyl)ethyl]-4,6-di-tert-butyl-2-methyl-2,3-dihydrobenzofuran (17.3 g) was dissolved in 80% acetic acid (150 ml) and the solution was heated under reflux for 1 h. After cooling the solution, the acetic acid was distilled off under vacuum and, after addition of water, the resulting mixture was extracted with ethyl acetate. The organic layer was washed with water and saturated brine, then dried over anhydrous magnesium sulfate and concentrated. The concentrate was purified by silica gel chromatography (25% ethyl acetate in n-hexane) to afford 5-acetoxy-4,6-di-tert-butyl-2-(2-formylethyl)-2-methyl-2,3-dihydrobenzofuran quantitatively (15.53 g) as a colorless oil.

$^1$H NMR (270 MHz, CDCl$_3$) δ ppm 1.30(s,9H), 1.37(s, 9H), 1.39(s,3H), 1.91–2.12(m,2H ), 2.30(s,3H), 2.59(q,2H), 3.13–3.32(m,2H), 6.71(s,1H), 9.78(s,1H) Mass 360(M$^+$)

Example 28

Synthesis of
5-Acetoxy-4,6-Di-tert-Butyl-2-(4-Ethoxycarbonyl-4-Methyl-3(E)-Butenyl)-2-Methyl-2,3-Dihydrobenzofuran 5-Acetoxy-4,6-di-tert-butyl-2-(2-formylethyl)-2-methyl-2,3-dihydrobenzofuran (15.5 g) and ethyl 2-(triphenylphosphoranylidene)propionate (32.4 g) were dissolved in benzene (250 ml) and the solution was heated under reflux for 1 h. After cooling, the solution was subjected to extraction with ethyl acetate and the organic layer was washed with water and saturated brine, then dried over anhydrous magnesium sulfate and concentrated. The concentrate was purified by silica gel chromatography (10% diethyl ether in n-hexane) to afford a mixture (2.4 g) containing 27% Z-form and 5-acetoxy-4,6-di-tert-butyl-2-(4-ethoxycarbonyl-4-methyl-3(E)-butenyl)-2-methyl-2,3-dihydrobenzofuran (13.2 g) as a colorless oil.

$^1$H NMR (270 MHz, CDCl$_3$) δ ppm 1.28(t,3H,J=7,3 Hz), 1.30(s,9H), 1.37(s,9H), 1.41(s,3H), 1.74–1.88(m,2H), 1.81(d,3H), 2.21–2.36(m,2H), 2.30(s,3H), 3.11–3.34(m, 2H), 4.18(q,2H,J=7.3 Hz), 6.73(s,1H), 6.72–6.78(m,1H) Mass 444(M$^+$)

Example 29

Synthesis of
5-Acetoxy-4,6-Di-tert-Butyl-2-(5-Hydroxy-4-Methyl-3(E)-Pentenyl)-2-Methyl-2,3-Dihydrobenzofuran 5-Acetoxy-4,6-di-tert-butyl-2-(4-ethoxycarbonyl-4-methyl-3(E)-butenyl)-2-methyl-2,3-dihydrobenzofuran (13.2 g) was dissolved in benzene (250 ml) and a tetrahydrofuran solution (60 ml) of 1M diisobutylaluminum hydride was added dropwise to the solution under cooling with ice. After stirring the mixture for 1 h, a saturated aqueous solution of ammonium chloride was added and the mixture was subjected to extraction with ethyl acetate. The organic layer was washed with water and saturated brine, dried over anhydrous magnesium sulfate and concentrated. The concentrate was purified by silica gel chromatography (33% ethyl acetate in n-hexane) to afford 5-acetoxy-4,6-di-tert-butyl-2-(5-hydroxy-4-methyl-3(E)-pentenyl)-2-methyl-2,3-dihydrobenzofuran [3.9 g (yield, 33%)] as a colorless oil. In addition, 4,6-di-tert-butyl-5-hydroxy-2-(5-hydroxy-4-methyl-3(E)-pentenyl)-2-methyl-2,3-dihydrobenzofuran [4.2 g (yield, 39%)] was obtained as a colorless oil.

5-Acetoxy-4,6-Di-tert-Butyl-2-(5-Hydroxy-4-Methyl-3(E)-Pentenyl-2-Methyl-2,3-Dihydrobenzofuran $^1$H NMR (270 MHz, CDCl$_3$) δ ppm 1.30(s,9H), 1.37(s, 9H), 1.44(s,3H), 1.64(d,3H), 1.68–1.80(m,2H), 2.05–2.22(m,2H), 2.29(s,3H), 3.08–3.34(m,2H), 3.97(bs, 2H), 5.41(m,1H), 6.73(s,1H) Mass 402(M$^+$)

4,6-Di-tert-Butyl-5-Hydroxy-2-(5-Hydroxy-4-Methyl-3(E)-Pentenyl)-2-Methyl-2-2,3-Dihydrobenzofuran $^1$H NMR (270 MHz, CDCl$_3$) δ ppm 1.39(s,3H), 1.41(s, 9H), 1.49(s,9H), 1.65(s,3H), 1.69–1.76(m,2H), 2.12–2.20(m,2H), 3.17(d,1H,J=15.5 Hz), 3.30(d,1H,J=15.5 Hz), 3.98(bs,2H), 4.70(s,1H), 5.42(m,1H), 6.63(s,1H) Mass 360(M$^+$)

IR (cm$^{-1}$) 3648, 3440, 2964

Example 30

Synthesis of
5-Acetoxy-2-(5-Chloro-4-Methyl-3(E)-Pentenyl)-4,6-Di-tert-Butyl-2-Methyl-2,3-Dihydrobenzofuran N-Chlorosuccinimide (150 mg) was suspended in dichloromethane (4 ml). After adding dimethyl sulfide (0.1 ml) dropwise at −5° C., the suspension was stirred for 15 min.

Subsequently, a solution of 5-acetoxy-4,6-di-tert-butyl-2-(5-hydroxy-4-methyl-3(E)-pentenyl)-2-methyl-2,3-dihydrobenzofuran (0.4 g) in dichloromethane (1 ml) was added dropwise and the resulting mixture was stirred at −5° C. for 90 min. After the end of the reaction, dichloromethane was distilled off under reduced pressure and the concentrate was purified by silica gel chromatography (25% ethyl acetate in n-hexane) to afford 5-acetoxy-2-(5-chloro-4-methyl-3(E)-pentenyl)-4,6-di-tert-butyl-2-methyl-2,3-dihydrobenzofuran [0.3 g (yield, 70%)] as a colorless oil.

$^1$H NMR (270 MHz, CDCl$_3$) δ ppm 1.30(s,9H), 1.37(s, 9H), 1.43(s,3H), 1.72(d,3H), 1.78(m,2H), 2.17(m,2H), 2.29(s,3H), 3.15–3.34(m,2H), 3.98(s,2H), 5.53(m,1H), 6.73(s,1H) Mass 422(M+2), 420(M$^+$)

Example 31

Synthesis of 5-Acetoxy-4,6-Di-tert-Butyl-2-Methyl-2-(6-p-Toluenesulfonyl-4,8,12-Trimethyltrideca-3(E),7(E),11-Trienyl)-2,3-Dihydrobenzofuran 3,7-Dimethyl-1-(p-toluenesulfonyl)-2(E),6-octadiene (0.26 g) synthesized in the usual manner was dissolved in a solvent system (2 ml) consisting of a 4:1 mixture of tetrahydrofuran and hexamethylphosphoric triamide. After adding a pentane solution (0.55 ml) of 1.6M n-butyllithium at −78° C., the mixture was stirred for 2 h. Subsequently, a solution of 5-acetoxy-2-(5-chloro-4-methyl-3(E)-pentenyl)4,6-di-tert-butyl-2-methyl-2,3-dihydrobenzofuran (0.3 g) in tetrahydrofuran (1 ml) was added dropwise at −78° C. and the mixture was stirred for 4 h. After the end of the reaction, a saturated aqueous solution of ammonium chloride was added and the resulting mixture was extracted with ethyl acetate. The organic layer was washed with water and saturated brine, then dried over anhydrous magnesium sulfate, and concentrated. The concentrate was purified by silica gel chromatography (25% ethyl acetate in n-hexane) to afford 5-acetoxy-4,6-di-tert-butyl-2-methyl-2-(6-p-toluenesulfonyl-4,8,12-trimethyltrideca-3(E),7(E),11-trienyl)-2,3-dihydrobenzofuran [0.26 g (yield, 55%)] as a colorless oil.

$^1$H NMR (270 MHz, CDCl$_3$) δ ppm 1.21(s,3H), 1.29(s, 9H), 1.36(s,9H), 1.39(s,3H), 1.47(m,4H), 1.52(s,3H), 1.58(s,3H), 1.67(s,3H), 1.93–2.12(m,4H), 2.22(d,1H), 2.29(s,3H), 2.42(s,3H), 2.85(d,1H), 3.17(m,2H), 3.87(m,1H), 4.88(d,1H), 5.02(m,1H), 5.15(m,1H), 6.71(s,1H), 7.29(d,2H,J=7.26 Hz), 7.71(d,2H,J=7.26 Hz) Mass 676(M$^+$)

Example 32

Synthesis of 5-Acetoxy-4,6-Di-tert-Butyl-2-Methyl-2-(4,8,12-Trimethyltrideca-3(E),7(E),11-Trienyl)-2,3-Dihydrobenzofuran 5-Acetoxy-4,6-di-tert-butyl-2-(6-p-toluenesulfonyl-4,8,12-trimethyltrideca-3(E),7(E),11-trienyl)-2,3-dihydrobenzofuran (0.26 g) was dissolved in tetrahydrofuran (2 ml) under a nitrogen atmosphere. Palladium chloride [1,4-bis-(diphenylphosphono)butane] complex (23 mg) prepared in the usual manner was added to the solution at 0° C.; thereafter, a tetrahydrofuran solution (0.76 ml) of 1M lithium triethylborohydride was added dropwise and the mixture was stirred for 24 h at −20° C. After the end of the reaction, a saturated aqueous solution of ammonium chloride was added the resulting mixture was extracted with ethyl acetate. The organic layer was washed with water and saturated brine, dried over anhydrous magnesium and concentrated. The concentrate was purified by silica gel chromatography (10% ethyl acetate in n-hexane) to afford 5-acetoxy-4,6-di-tert-butyl-2-methyl-2-(4,8,12-trimethyltrideca-3(E),7(E),11-trienyl)-2,3-dihydrobenzofuran [0.11 g (yield, 55%)] as a colorless oil.

$^1$H NMR (270 MHz, CDCl$_3$) δ ppm 1.30(s,9H), 1.37(s, 12H), 1.43(s,3H), 1.59(s,6H), 1.67(s,3H), 1.98–2.11(m, 12H), 2.29(s,3H), 3.07–3.35(m,2H), 5.10(m,3H), 6.73(s,1H) Mass 522(M$^+$)

Example 33

Synthesis of 4,6-Di-tert-Butyl-5-Hydroxy-2-Methyl-2-(4,8,12-Trimethyltrideca-3(E),7(E),11-Trienyl)-2,3-Dihydrobenzofuran (Compound α)

Lithium aluminum hydride (8 mg) was suspended in tetrahydrofuran (3 ml) under a nitrogen atmosphere. A solution of 5-acetoxy-4,6-di-tert-butyl-2-methyl-2-(4,8,12-trimethyltrideca-3(E),7(E),11-trienyl)-2,3-dihydrobenzofuran (0.11 g) in tetrahydrofuran (2 ml) was added dropwise to the suspension under cooling with ice. After heating under reflux for 3 h, the mixture was cooled to room temperature and water was added dropwise. Following addition of 10% aqueous HCl, the mixture was subjected to extraction with ethyl acetate. The organic layer was dried over anhydrous magnesium sulfate and concentrated. The concentrate was purified by silica gel chromatography (n-hexane) to afford 4,6-di-tert-butyl-5-hydroxy-2-methyl-2-(4,8,12-trimethyltrideca-3(E),7(E),11-trienyl)-2,3-dihydrobenzofuran [70 mg (yield, 69%)] as a colorless oil.

$^1$H NMR (270 MHz, CDCl$_3$) δ ppm 1.38(s,3H), 1.41(s, 9H), 1.43(s,3H), 1.49(s,9H), 1.59(s,6H), 1.67(s,3H), 1.90–2.14(m,12H), 3.15(d,1H,J=15.7 Hz), 3.31(d,1H,J=15.7 Hz), 4.68(s,1H), 5.10(m,3H), 6.63(s,1H) Mass 480(M$^+$)

IR (cm$^{-1}$) 3648, 2964

INDUSTRIAL APPLICABILITY

The compounds of the invention that are represented by the general formula (I) have a highly selective antioxidative activity and are useful as therapeutics of ischemic diseases such as myocardial infarction, cerebral apoplexy and arteriosclerosis. The compounds of the invention that are represented by the general formula (II) are intermediates suitable for producing the compounds of the general formula (I).

We claim:

1. A compound represented by the formula (I):

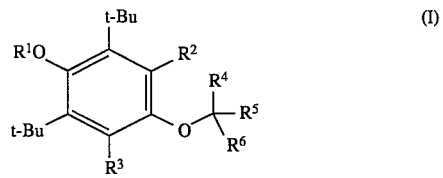

where $R^1$ is a hydrogen atom or an acyl group; $R^3$ is a hydrogen atom or a lower alkyl group; $R^5$ and $R^6$ which may be the same or different are a hydrogen atom or an optionally substituted alkyl, alkenyl, alkynyl or aryl group; and $R^2$ and $R^4$ taken together form a dihyrobenzofuran ring.

2. A compound according to claim 1 wherein $R^1$ is acetyl.

3. A compound according to claim 1 wherein at least one of $R^5$ and $R^6$ is a straight or branched optionally substituted alkyl group having 1–20 carbon atoms, a straight or branched optionally substituted alkenyl group having 2–20 carbon atoms, or a straight or branched optionally substituted alkynyl group having 2–20 carbon atoms.

4. A compound as claimed in claim 1 which is represented by formula (I) wherein $R^1$ is a hydrogen atom; and $R^3$ is a hydrogen atom or a straight or branched alkyl group having 1–4 carbon atoms.

5. A compound as claimed in claim 1 which is represented by formula (I) wherein $R^1$ is a hydrogen atom; $R^3$ is a hydrogen atom or a straight or branched alkyl group having 1–4 carbon atoms; and $R^5$ and $R^6$, which may be the same or different, are an optionally substituted alkyl, alkenyl or aryl group having 2–20 carbon atoms.

6. A compound as claimed in claim 1 which is selected from the group consisting of:
4,6-di-tert-butyl-5-hydroxy-2,3-dihydrobenzofuran,
4,6-di-tert-butyl-5-hydroxy-2-methyl-2,3-dihydrobenzofuran,
4,6-di-tert-butyl-5-hydroxy-2,2-dimethyl-2,3-dihydrobenzofuran,
4,6-di-tert-butyl-5-hydroxy-2,2-diethyl-2,3-dihydrobenzofuran,
4,6-di-tert-butyl-5-hydroxy-2,2-di-n-propyl-2,3-dihydrobenzofuran,
4,6-di-tert-butyl-5-hydroxy-2,2-di-n-butyl-2,3-dihydrobenzofuran,
4,6-di-tert-butyl-5-hydroxy-2-octyl-2,3-dihydrobenzofuran,
2,4,6-tri-tert-butyl-5-hydroxy-2,3-dihydrobenzofuran,
4,6-di-tert-butyl-2,2-di-i-propyl-5-hydroxy-2,3-dihydrobenzofuran,
4,6-di-tert-butyl-2,2-diphenyl-5-hydroxy-2,3-dihydrobenzofuran,
4,6-di-tert-butyl-2,2-dibenzyl-5-hydroxy-2,3-dihydrobenzofuran,
4,6-di-tert-butyl-2-chloromethyl-5-hydroxy-2,3-dihydrobenzofuran,
5-hydroxy-4,6-di-tert-butyl-2,2-dimethyl-7-n-propyl-2,3-dihydrobenzofuran,
2,4,6-tri-tert-butyl-5-hydroxybenzofuran,
4,6-di-tert-butyl-2,2-di-n-pentyl-5-hydroxy-2,3-dihydrobenzofuran,
4,6-di-tert-butyl-2,2-di-n-octyl-5-hydroxy-2,3-dihydrobenzofuran,
2,2-diisoamyl-4,6-di-tert-butyl-5-hydroxy-2,3-dihydrobenzofuran,
4,6-di-tert-butyl-5-hydroxy-2-methyl-2-(4',8',12'-trimethyl-trideca-3'(E),7'(E),11'-trienyl)-2,3-dihydrobenzofuran,
4,6-di-tert-butyl-2,2-di-n-heptyl-5-hydroxy-2,3-dihydrobenzofuran,
4,6-di-tert-butyl-2,2-di-n-hexyl-5-hydroxy-2,3-dihydrobenzofuran,
4,6-di-tert-butyl-5-hydroxy-2-methyl-2-(4',8',12'-trimethyl-tridecyl)-2,3-dihydrobenzofuran, and
4,6-di-tert-butyl-5-hydroxy-2-(5'-hydroxy-4'-methyl-3'(E)-pentenyl)-2-methyl-2,3-dihydrobenzofuran.

7. A compound as claimed in claim 1 which is selected from the group consisting of:
4,6-di-tert-butyl-5-hydroxy-2,3-dihydrobenzofuran,
4,6-di-tert-butyl-5-hydroxy-2-methyl-2,3-dihydrobenzofuran,
4,6-di-tert-butyl-5-hydroxy-2,2-dimethyl-2,3-dihydrobenzofuran,
4,6-di-tert-butyl-5-hydroxy-2,2-diethyl-2,3-dihydrobenzofuran,
4,6-di-tert-butyl-5-hydroxy-2,2-di-n-propyl-2,3-dihydrobenzofuran,
4,6-di-tert-butyl-5-hydroxy-2,2-di-n-butyl-2,3-dihydrobenzofuran,
4,6-di-tert-butyl-5-hydroxy-2-octyl-2,3-dihydrobenzofuran,
2,4,6-tri-tert-butyl-5-hydroxy-2,3-dihydrobenzofuran,
4,6-di-tert-butyl-2,2-di-i-propyl-5-hydroxy-2,3-dihydrobenzofuran,
4,6-di-tert-butyl-2,2-diphenyl-5-hydroxy-2,3-dihydrobenzofuran,
4,6-di-tert-butyl-2,2-dibenzyl-5-hydroxy-2,3-dihydrobenzofuran,
4,6-di-tert-butyl-2-chloromethyl-5-hydroxy-2,3-dihydrobenzofuran,
5-hydroxy-4,6-di-tert-butyl-2,2-dimethyl-7-n-propyl-2,3-dihydrobenzofuran,
4,6-di-tert-butyl-2,2-di-n-pentyl-5-hydroxy-2,3-dihydrobenzofuran,
4,6-di-tert-butyl-2,2-di-n-octyl-5-hydroxy-2,3-dihydrobenzofuran,
2,2-diisoamyl-4,6-di-tert-butyl-5-hydroxy-2,3-dihydrobenzofuran,
4,6-di-tert-butyl-5-hydroxy-2-methyl-2-(4',8',12'-trimethyl-trideca-3'(E),7'(E),11'-trienyl)-2,3-dihydrobenzofuran,
4,6-di-tert-butyl-2,2-di-n-heptyl-5-hydroxy-2,3-dihydrobenzofuran,
4,6-di-tert-butyl-2,2-di-n-hexyl-5-hydroxy-2,3-dihydrobenzofuran,
4,6-di-tert-butyl-5-hydroxy-2-methyl-2-(4',8',12'-trimethyl-tridecyl)-2,3-dihydrobenzofuran, and
4,6-di-tert-butyl-5-hydroxy-2-(5'-hydroxy-4'-methyl-3'(E)-pentenyl)-2-methyl-2,3-dihydrobenzofuran.

8. A compound according to claim 1 wherein at least one of $R^5$ and $R^6$ is an alkyl group of 1–20 carbons, an alkenyl of 2–20 carbons or an alkynyl of 2–20 carbons.

9. A process for producing a compound represented by formula (I):

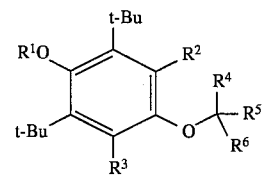

wherein $R^1$ is a hydrogen atom or an acyl group; $R^3$ is a hydrogen atom or a lower alkyl group; $R^2$ and $R^4$ taken together form a dihydrobenzofuran ring; $R^5$ and $R^6$, which may be the same or different, are a hydrogen atom or an optionally substituted alkyl, alkenyl or aryl group, which comprises the steps of (a) treating a compound of formula (II):

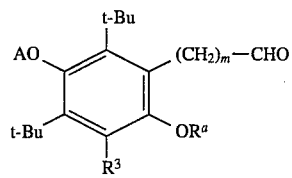

wherein $R^3$ has the same meaning as defined above; A is a protective group; $R^a$ is a hydrogen atom; and m is an integer of 0, with a Grignard reagent, an organolithium compound and the like to afford the compound of formula (32) or (33):

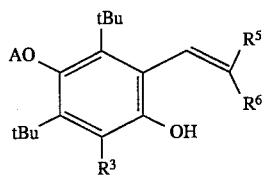
(32)

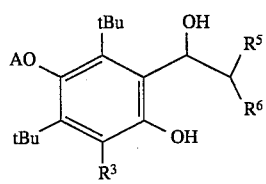
(33)

(b) dissolving the compound of formula (32) or (33) in a solvent to afford a solution thereof;
(c) allowing a Lewis acid to act on the solution to afford the compound of formula (34):

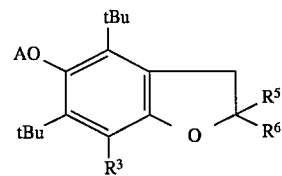
(34)

(d) optionally deprotecting the compound of formula (34) by a conventional method to yield the compound of formula (35):

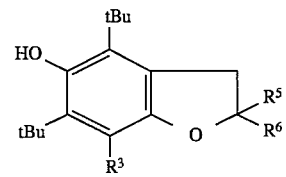
(35)

* * * * *

UNITED STATES PATENT AND TRADEMARK OFFICE
CERTIFICATE OF CORRECTION

PATENT NO. : 5,574,178
DATED : 11/12/96
INVENTOR(S) : Tamura et al.

It is certified that error appears in the above-indentified patent and that said Letters Patent is hereby corrected as shown below:

Column 47, line 41, delete "2,4,6-tri-tert-butyl-5-hydroxybenzofuran,"

Signed and Sealed this

Eighteenth Day of February, 1997

*Attest:*

BRUCE LEHMAN

*Attesting Officer*  *Commissioner of Patents and Trademarks*